United States Patent
Kumar et al.

(10) Patent No.: US 9,446,019 B2
(45) Date of Patent: Sep. 20, 2016

(54) SPARSTOLONIN B BASED PHARMACEUTICAL AGENT FOR NEUROBLASTOMA TREATMENT

(71) Applicant: University of South Carolina, Columbia, SC (US)

(72) Inventors: Ambrish Kumar, Columbia, SC (US); Ugra Sen Singh, Columbia, SC (US); Daping Fan, Columbia, SC (US); Donald J. Dipette, Blythewood, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 14/483,445

(22) Filed: Sep. 11, 2014

(65) Prior Publication Data

US 2015/0105454 A1    Apr. 16, 2015

Related U.S. Application Data

(60) Provisional application No. 61/960,259, filed on Sep. 13, 2013.

(51) Int. Cl.
| | |
|---|---|
| *A01N 43/16* | (2006.01) |
| *A61K 31/35* | (2006.01) |
| *A61K 31/353* | (2006.01) |
| *A61K 31/37* | (2006.01) |

(52) U.S. Cl.
CPC ............ *A61K 31/353* (2013.01); *A61K 31/37* (2013.01)

(58) Field of Classification Search
None
See application file for complete search history.

(56) References Cited

U.S. PATENT DOCUMENTS

| | | |
|---|---|---|
| 2014/0107354 A1 | 4/2014 | Wang et al. |
| 2014/0303242 A1 | 10/2014 | Fan et al. |

FOREIGN PATENT DOCUMENTS

| | | | |
|---|---|---|---|
| CN | 102218058 A | 10/2011 | |
| IL | WO 2009015107 A1 * | 1/2009 | ............. A61K 31/70 |

OTHER PUBLICATIONS

Liang et al., "Characterization of Sparstolonin B, a Chinese Herb-derived Compound, as a Selective Toll-Like Receptor Antagonist with Potent Anti-inflammatory Properties," Journal of Biological Chemistry, vol. 286, No. 30, Jul. 29, 2011.*
Li, S.X., et al., *A new alkaloid from the stem of Sparganium stoloniferum Buch.-Ham.* J. Asian Nat. Prod. Res. 12(4): p. 331-333.
Lin, et al., *Xanthone derivatives as potential anti-cancer drugs.* Journal of Pharmacy and pharmacology (1996) 48, 539-544.
Na, et al., *Recent cancer drug development with xanthone structures.* J Pharm Pharmacol (2009) 61: 707-712.
Xiong et al., *New chemical constituents from the rhizomes of Sparganium stoloniferum.* Arch Pharm Res (2009) 32: 717-720.
Lee, S.Y., et al., *A new phenylpropane glycosides from the rhizome of Sparganium stoloniferum.* Arch. Pharm. Res. 33(4): p. 515-21.
Sun, J., S. Wang, and Y.H. Wei, *Reproductive toxicity of Rhizoma Sparganii (Sparganium stoloniferum Buch.-Ham.) in mice: mechanisms of anti-angiogenesis and anti-estrogen pharmacologic activities.* J Ethnopharmacol, 2011. 137(3): p. 1498-503.
Wu, H., et al., *Rapid preparative isolation of a new phenylpropanoid glycoside and four minor compounds from Sparganium stoloniferum using high-speed counter-current chromatography as a fractionation tool.* J Sep Sci, 2012. 35(9): p. 1160-6.
Qin, G.W. and R.S. Xu, *Recent advances on bioactive natural products from Chinese medicinal plants.* Med Res Rev, 1998. 18(6): p. 375-82.
Zhou, L.G. and J.Y. Wu, *Development and application of medicinal plant tissue cultures for production of drugs and herbal medicinals in China.* Nat Prod Rep, 2006. 23(5): p. 789-810.
Liang, et al. *Sparstolonin B suppresses lipopolysaccharide-induced inflammation in human umbilical vein endothelial cells.* (2013) Arch Pharm Res 36: 890-896.
Riveiro, et al., *Coumarins: old compounds with novel promising therapeutic perspectives.* (2010) Curr Med Chem 17: 1325-1338.
Wu, et al., *The structure and pharmacological functions of coumarins and their derivatives.* (2009) Curr Med Chem 16: 4236-4260.

* cited by examiner

*Primary Examiner* — Jared D Barsky
(74) *Attorney, Agent, or Firm* — Dority & Manning, P.A.

(57) ABSTRACT

Use of sparstolonin B in inhibition of growth and/or viability of human neuroblastoma cells is described. The sparstolonin B can be naturally derived from the Chinese herb *Sparganium stoloniferum* or can be synthetic. The sparstolonin B is shown to be effective both in vitro and in vivo in inhibition of growth and/or viability of neuroblastoma cells of multiple different genetic backgrounds including N-myc amplified with wild p53 neuroblastoma cells, N-myc amplified with mutated p53 neuroblastoma cells, and N-myc nonamplified neuroblastoma cells.

18 Claims, 18 Drawing Sheets

SPARSTOLONIN B BASED PHARMACEUTICAL AGENT FOR NEUROBLASTOMA TREATMENT

CROSS REFERENCE TO RELATED APPLICATION

This application claims filing benefit of U.S. Provisional Patent Application Ser. No. 61/960,259 having a filing date of Sep. 13, 2013, which is incorporated herein in its entirety.

GOVERNMENT SUPPORT CLAUSE

This invention was made with government support under R21AA016121, R21AT006767 and R01HL116626 awarded by the National Institutes of Health. The government has certain rights in the invention.

BACKGROUND

Neuroblastoma is a malignant cancer of the postganglionic sympathetic nervous system that commonly presents in childhood and is derived from the neural crest cells during embryonic development. Initially it develops in the adrenal gland and metastasizes to liver, bone, bone marrow, lymph nodes, neck and chest. It is the most common cancer in babies younger than one and the second most common tumor in children. In the United State, approximately 700 children are diagnosed with neuroblastoma each year. It accounts for 7% of all childhood cancers, and is responsible for 15% of all cancer deaths in children younger than 15 years. Despite standard therapy for advanced disease including chemotherapy, surgery, and radiation, the mortality rate remains high for these patients. The five-year survival rate for children with low-risk neuroblastoma is higher than 95%, and for children with intermediate-risk neuroblastoma the survival rate is 80% to 90%, but only about 30% to 50% of children with high-risk neuroblastoma experience long-term survival.

Neuroblastoma tumor comprises populations of various heterogeneous cells including N-type cells (neuroblastic), S-type cells (substrate adherent) and I-type cells (intermediate). These cells differ at morphological and biochemical levels. N-type cells are neuroblastic with a small, rounded, loosely adherent cell body and numerous neurite-like processes. S-type cells are highly substrate adherent with a larger, flattened epithelial-like cell body. I-type cells represent a cellular intermediate in the N-type and S-type cell transdifferentiation process. At biochemical levels, S-type cells do not exhibit neuronal properties such as neurotransmitter biosynthetic enzyme activities, catecholamine uptake, or receptor proteins as do N-type cells. N-type and I-type cells express neurofilament proteins while I-type and S-type cells are more strongly positive for vimentin than N-type cells.

The most common cytogenetic features identified in low to advance stages of neuroblastoma include genomic amplification of MYCN gene, rearrangement or deletion of distal region of the chromosome 1 (1p31-arm), or alterations in chromosomes 11, 14 and 17. Mutations in tumor suppresser genes, i.e., p53, retinoblastoma, RET, p16, p18 or p27 have been reported as promoting tumerogenesis. These karyotype and cytogenetic alterations develop drug resistance and protect tumors against the available chemotherapies. For example, retinoic acid induces neuronal differentiation in neuroblastoma cells and is commonly used in residual therapy. However, neuroblastoma cells with MYCN-amplified oncogene do not respond to retinoic acid.

Sparstolonin B (SsnB) has been isolated from the tubers of an aquatic herb, *Sparganium stoloniferum*. SsnB has been shown to act as antagonist to Toll-like Receptors 2 and 4 (TLR2 and TLR4), and can exhibit anti-inflammatory properties by selectively inhibiting TLR2 and TLR4-triggered inflammatory response in mouse and human macrophages. In traditional Chinese medicine, the tubers of this herb have been used for the treatment of several inflammatory diseases. In addition, the crude extract prepared form this herb can have anti-spasmodic and certain anti-tumor properties.

What is needed in the art are targeted agents and combination chemotherapy in the treatment of neuroblastoma tumors.

SUMMARY

According to one embodiment, a method for inhibiting the growth and/or viability of neuroblastoma cells is described. For example, the method can include contacting neuroblastoma cells with sparstolonin B (SsnB), the sparstolonin B contacting the cells at a concentration of about 10 micromolar ($\mu M$) or greater. For instance, in one particular embodiment, disclosed is a method for treatment of neuroblastoma that includes administering a purified SsnB to a person suffering from neuroblastoma such that SsnB at a concentration of about 10 $\mu M$ or greater contacts the cells.

BRIEF DESCRIPTION OF THE FIGURES

FIG. 4A includes representative Western blots for N-myc protein in total cell extract prepared from IMR-32, NGP and SK-N-BE(2) cells treated with or without SsnB (1 μM or 10 μM) for 2 days, 3 days or 4 days, respectively. β-actin was used to check loading differences. FIG. 4B is a bar diagram representing the fold change in N-myc protein signals as measured by imageJ programme. Bar represents mean and S.D. of three independent experiments and *$p<0.05$, SsnB 10 μM vs control; ns=nonsignificant vs. control.

DETAILED DESCRIPTION

Figure 1A:
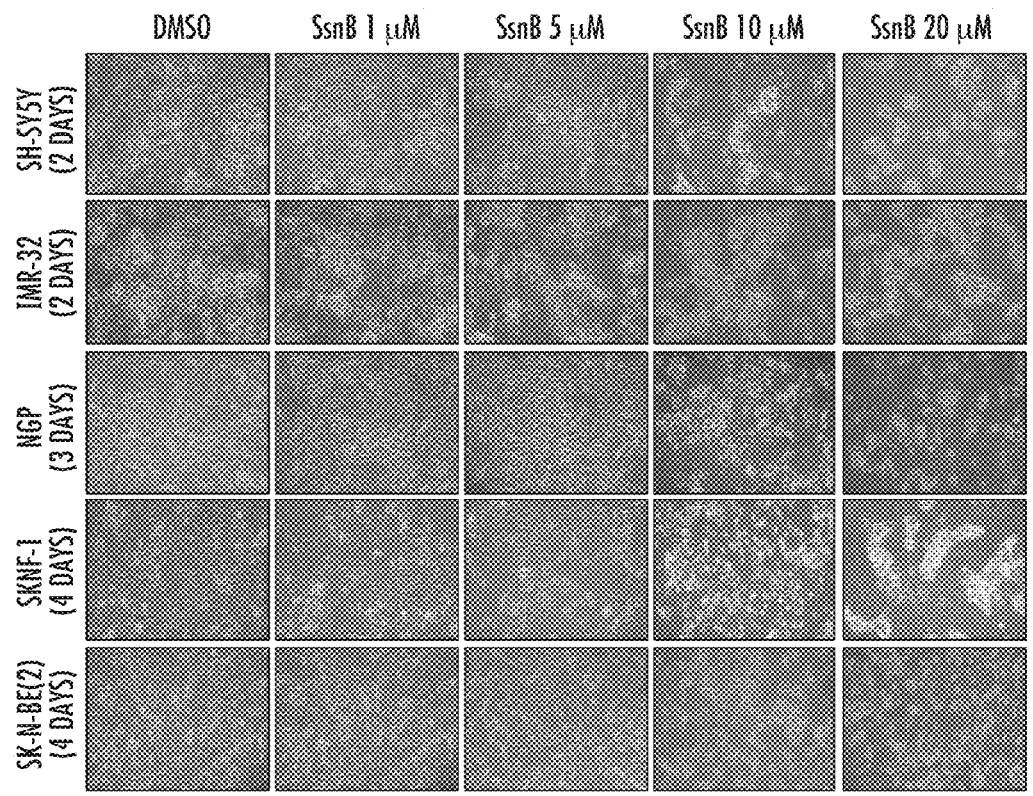
FIG. 1A provides phase contrast images showing the morphology of neuroblastoma cells including SH-SY5Y cells ($1^{st}$ row), IMR-32 cells ($2^{nd}$ row), NGP cells ($3^{rd}$ row), SKNF-1 cells ($4^{th}$ row) and SK-N-BE(2) cells ($5^{th}$ row) after treatment with SsnB 1 $\mu M$ ($2^{nd}$ column), 5 $\mu M$ ($3^{rd}$ column), 10 $\mu M$ ($4^{th}$ column), and 20 $\mu M$ ($5^{th}$ column) or with DMSO ($1^{st}$ column). Cells treated with similar volume of dimethyl sulfoxide (DMSO) were used as control. Images were taken at the indicated times.

The following description and other modifications and variations to the present invention may be practiced by those of ordinary skill in the art, without departing from the spirit and scope of the present invention. In addition, it should be understood that aspects of the various embodiments may be interchanged both in whole and in part. Furthermore, those of ordinary skill in the art will appreciate that the following description is by way of example only, and is not intended to limit the invention.

According to the present disclosure, Sparstolonin B (SsnB) has been found efficacious in treatment and study of neuroblastoma. Thus, the present disclosure is directed in one embodiment to the utilization of SsnB in inhibiting the survival of human neuroblastoma cells of different genetic background such as N-myc amplified with wild p53 neuroblastoma cells, N-myc amplified with mutated p53 neuroblastoma cells, and N-myc nonamplified neuroblastoma cells.

Neuroblastoma tumors have a heterogeneous population of cells of different genetic background. Increasing evidence supports that molecular and genetic factors such as N-myc oncogene amplification, deletion of short arm of chromosome 1 and high expression of neurotrophin receptors (TrkA and TrkB) are associated with malignant transformation and progression of neuroblastoma. Despite focusing on new molecular targets and the use of multimodal therapy which includes surgery, radiotherapy in conjunction with chemotherapy and monoclonal antibody based immunotherapy; approximately 30% of children with high-risk neuroblastoma remain incurable. Hence, the utilization of SsnB as a therapeutic compound in treatment of neuroblastoma is needed, particularly as this naturally derived compound can exhibit less toxicity as compared to many previously known chemotherapeutic agents.

The naturally-occurring form of SsnB is isolated from the tubers of an aquatic Chinese herb, *Sparganium stoloniferum*. The structure of SsnB (8,5'-dihydroxy-4-phenyl-5,2'-oxidoisocoumarin) is as follows:

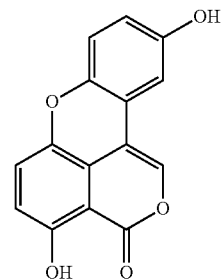 [SMILES: O=c1occ2c3c(ccc(O)c13)Oc1ccc(O)cc1-2]

SsnB for use as described can include the purified natural compound as well as synthetic formations of SsnB. Purified SsnB can be obtained from *S. stoloniferum* according to standard isolation and purification methods. For instance, SsnB can be extracted and purified to a level of about 90% or high purification, about 95% or higher purification, about 99% or higher purification, or 100% pure, with little or no amounts of additional compounds in combination with the purified SsnB. Those compounds that can be included in small amounts in the purified SsnB formulation can include both natural compounds carried over with the SsnB from the *S. stoloniferum* as well as compounds utilized in extracting the SsnB from the *S. stoloniferum*.

Synthetic SsnB is also encompassed herein. SsnB has structural similarities to isocoumarins and xanthones. Thus, in one embodiment, synthetic SsnB can be formed according to methods known in the art for forming isocoumarins and/or xanthones. For instance, in one embodiment a synthetic SsnB can be formed according to methods as described in U.S. Published Patent Application No. 2014/0107354 to Wang, et al., which is incorporated herein by reference. Briefly, a method can include reacting a 2-substituted benzaldehyde with a suitable phenol derivative to form the synthetic SsnB.

It should be understood that the purified natural or synthetic SsnB can be combined with other materials as discussed further herein in forming a treatment or study composition. Purified SsnB is a starting compound that can be used either alone or in combination with other compounds for use as described herein. A treatment or study composition is not intended to be limited to containing only the purified SsnB.

The SsnB can be provided to a neuroblastoma cell at a concentration of about 10 μM or more and inhibit the growth and viability of the cell. For instance, the SsnB can be provided to neuroblastoma cells at a concentration of from about 10 μM to about 100 μM and inhibit the growth and viability of the cells with little or no detrimental effect to surrounding healthy cells. Beneficially, it is believed that SsnB exerts its inhibitory effects only in neuroblastoma cell lines, and up to an about 100 μM concentration, the SsnB will not exhibit cytotoxicity towards normal non-tumor human cells such as human monocytic THP-1 cells, phorbol 12-myristate 13-acetate-differentiated THP-1 macrophages, human umbilical vein endothelial cells and human aortic smooth muscle cells.

SsnB at about 10 µM and above concentrations can significantly inhibit the growth and viability of human neuroblastoma cells of different genetic background such as N-myc amplified with wild p53 cells (IMR-32 and NGP cells), N-myc amplified with mutated p53 cells (SKN-BE(2) cell), and N-myc nonamplified cell (SH-SY5Y and SKNF-1 cells). While SsnB can be effective against different type of neuroblastoma cells, the sensitivity of the different types of neuroblastoma cells toward SsnB can vary. For instance, SH-SY5Y and IMR-32 cells are generally highly sensitive, NGP cells are generally moderate sensitive, and SKNF-1 and SK-N-BE(2) cells can show a lower sensitive. As such, the specific concentration at which the SsnB is delivered to neuroblastoma cells can vary depending upon the specific cell types and ratios of cell types included in the targeted tumor or culture.

Without wishing to be bound to any particular theory, it is believed that the reduced viability by SsnB affects the neuroblastoma cells' ability to form compact spheroids, which decreases the tumorigenic potential of both N-myc amplified (e.g., SK– N-BE(2) cells) and N-myc non-amplified neuroblastoma cells (e.g., SH-SY5Y cells).

The inhibitory effect of SsnB on cell growth and viability is believed to result from caspase-mediated cell death. As is known, increased level of the activated form of caspase-3 has been shown to trigger DNA fragmentation, chromatin condensation, membrane blebbing and cell shrinkage that leads to the programme cell death (apoptosis). SsnB-treated neuroblastoma cells can exhibit higher levels of apoptosis as compared to control cells, and indications are that SsnB triggers apoptotic cell death pathways via activation of a caspase cascade.

SsnB can also promote generation of reactive oxygen species (ROS) in both N-myc amplified and N-myc non-amplified neuroblastoma cells. ROS such as free radicals and peroxides can increase cellular oxidative stress, which can in turn promote lipid peroxidation and oxidation of nucleic acid thus amplifying cell death. An imbalance between the generation of ROS) and antioxidant defense status can disrupt the redox homeostasis, leading to cell death.

SsnB can also decrease the glutathione (GSH) level in neuroblastoma cells. GSH acts as an antioxidant and its role to remove oxidative stress caused by ROS is well known. Thus, GSH depletion due to the presence of SsnB will lead to failure of the cell to remove free radicals and this can be a primary cause of SsnB-induced cytotoxicity towards neuroblastoma cells.

The induction of cell cycle arrest at a specific checkpoint and thereby induction of apoptosis is a common mechanism for the cytotoxic effects of many anticancer drugs. For instance, cell cycle arrest at G2/M transition is a target for main cancer therapies as this can prevent DNA-damaged cells from entering mitosis. Cell cycle blockage at this checkpoint can be carried out by cell cycle-related proteins such as p53 and cyclins. It is known that activation of p53, a tumor suppressor protein, leads to growth arrest at G1 or G2 phase of cell cycle. In the presently disclosed methods, treatment of neuroblastoma cells with SsnB can lead to cell cycle block in G2/M phase and increase in expression of p53. Thus, p53-mediated apoptosis can also be a factor in SsnB-induced cytotoxicity for p53-containing neuroblastoma cells.

It is well known that N-myc amplification is associated with neuroblastoma tumor progression and drug resistance. N-myc, a member of the myc family of proto-oncoproteins, acts as a transcription factor and regulates the expression of genes involved in cell cycle, DNA damage and apoptosis.

Overexpression of N-myc in transgenic mice has previously been shown to result in neuroblastoma development, and down-regulation of N-myc expression has been shown to induce growth arrest and apoptosis in neuroblastoma cells. Disclosed SsnB treatment methods can suppress N-myc expression in neuroblastoma cells, which can be correlated with the SsnB-mediated anticancer activity toward human neuroblastoma cells.

Methods for treatment of neuroblastoma utilizing SsnB can generally include contacting neuroblastoma cells N-myc amplified with wild p53 cells, N-myc amplified with mutated p53 cells, and N-myc nonamplified cells with a composition comprising SsnB.

The methods can be utilized in vivo for treatment of neuroblastoma or in vitro for study of neuroblastoma cells. According to an in vivo treatment method, a composition including SsnB (e.g., purified natural SsnB or synthetic SsnB) and a pharmaceutically compatible carrier can be delivered to a patient via any pharmaceutically acceptable delivery system. For instance, a composition including a pharmaceutically compatible carrier and SsnB may be a solid, liquid or aerosol form and may be administered by any known pharmaceutically acceptable route of administration. The dosage amount can vary depending upon the specific state of the neuroblastoma. For instance, a dosage amount for a patient can be from about 5 mg/kg/day to about 20 mg/kg/day, for instance about 10 mg/kg/day in one embodiment.

A non-limiting exemplary listing of possible solid compositions can include pills, creams, and implantable dosage units. An implantable dosage unit can, in one embodiment, be administered locally, for example at a tumor site, or can be implanted for systemic release of the composition, for example subcutaneously. A non-limiting exemplary listing of possible liquid compositions can include formulations adapted for injection subcutaneously, intravenously, intra-arterially, and formulations for topical and intraocular administration. Possible examples of aerosol formulations include inhaler formulations for direct administration to the lungs.

Compositions can generally be administered by standard routes. For example, the compositions may be administered by topical, transdermal, intraperitoneal, intracranial, intra-cerebroventricular, intra-cerebral, intra-vaginal, intrauterine, oral, rectal or parenteral (e.g., intravenous, intra-spinal, subcutaneous or intramuscular) route. Osmotic mini-pumps may also be used to provide controlled delivery of SsnB through cannulae to the site of interest, such as directly into a metastatic growth.

Pharmaceutical compositions for parenteral injection can include pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. A composition can contain minor amounts of auxiliary substances such as wetting or emulsifying agents, pH buffering agents and the like that can enhance the effectiveness of the active ingredient. Proper fluidity may be maintained, for example, by the use of coating materials such as lecithin, by the maintenance of the required particle size in the case of dispersions and by the use of surfactants. A composition may also contain adjuvants such as preservatives, wetting agents, emulsifying agents and dispersing agents. Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

Prolonged absorption of an injectable pharmaceutical form may be brought about by the inclusion of agents, such as aluminum monostearate and gelatin, which can delay absorption. For example, injectable depot forms can be made by forming microencapsule matrices of the SsnB in biodegradable polymers such as polylactide-polyglycolide, poly(orthoesters) and poly(anhydrides). Depending upon the ratio of SsnB to polymer and the nature of the particular polymer employed, the rate of release can be controlled. Depot injectable formulations can also be prepared by entrapping the SsnB in liposomes or microemulsions that are compatible with body tissues. An injectable formulation may be sterilized, for example, by filtration through a bacterial-retaining filter or by incorporating sterilizing agents in the form of sterile solid compositions that can be dissolved or dispersed in sterile water or other sterile injectable media just prior to use.

A composition can include pharmaceutically acceptable salts of the components therein, e.g., those that may be derived from inorganic or organic acids. Pharmaceutically acceptable salts are well known in the art. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. The salts may be prepared in situ during the final isolation and purification of the SsnB or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptonoate, hexanoate, fumarate, hydrochloride, hydrobromide, hydroiodide, 2-hydroxymethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl, and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

A treatment method can include use of timed release or sustained release delivery systems as are generally known in the art. A sustained-release matrix can include a matrix made of materials, usually polymers, which are degradable by enzymatic or acid/base hydrolysis or by dissolution. Once inserted into the body, such a matrix can be acted upon by enzymes and body fluids. The sustained-release matrix desirably is chosen from biocompatible materials such as and without limitation to liposomes, polylactides (polylactic acid), polyglycolide (polymer of glycolic acid), polylactide co-glycolide (co-polymers of lactic acid and glycolic acid) polyanhydrides, poly(ortho)esters, polyproteins, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone.

When SsnB is administered orally, the therapeutic compositions can be in the form of a tablet, capsule, powder, solution or elixir. When administered in tablet form, a composition may additionally contain a solid carrier such as a gelatin or an adjuvant. A tablet, capsule, or powder can, for example, contain from about 5 to 95% by weight of SsnB. In one embodiment, a composition can contain from about 25 to 90% by weight of SsnB.

When administered orally in liquid form, a liquid carrier such as water, petroleum, oils of animal or plant origin such as peanut oil, mineral oil, soybean oil, or sesame oil, or synthetic oils may be added. A liquid form may further contain physiological saline solution, dextrose or other saccharide solution, or glycols such as ethylene glycol, propylene glycol or polyethylene glycol. When administered in liquid form, a composition can contain from about 0.5 to 90% by weight SsnB, in one embodiment from about 1 to 50% by weight SsnB.

When an effective amount of SsnB is administered by intravenous, cutaneous or subcutaneous injection, the SsnB composition can generally be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection can contain, in addition to the SsnB, an isotonic vehicle such as Sodium Chloride Injection, Ringer's Injection, Dextrose Injection, Dextrose and Sodium Chloride Injection, Lactated Ringer's Injection, or other vehicle as known in the art. The composition may also contain stabilizers, preservatives, buffers, antioxidants, or other additives known to those of skill in the art.

It is to be understood that the in vivo methods have application for both human and veterinary use. The methods of the present invention contemplate single as well as multiple administrations, given either simultaneously or over an extended period of time. In addition, SsnB can be administered in treatment of neuroblastoma in conjunction with other forms of therapy, e.g., and without limitation, chemotherapy, radiotherapy, or other immunotherapy, surgical intervention, and combinations thereof.

The present disclosure may be better understood with reference to the Examples, set forth below.

EXAMPLE 1

Human Neuroblastoma Cell Culture and SsnB Treatments

Human neuroblastoma cell lines (SH-SY5Y, IMR-32, SK-N-BE(2) and SKNF-1 cells) were obtained from The American Type Culture Collection (ATCC; Manassas, Va.), and NGP cells were kind gift from Garrett M. Brodeur (The Children's Hospital of Philadelphia, Philadelphia, Pa.). All cell lines were maintained in complete Dulbecco's Modified Eagle's Medium (DMEM) supplemented with 10% fetal bovine serum (FBS; Atlanta Biologicals, Lawrenceville, Ga.) and 1× antibiotic-antimycotic solution (containing 100 U/ml penicillin, 100 µg/ml streptomycin and 0.25 µg/ml amphotericin B), and grown at 37° C. in a humidified incubator with 5% $CO_2$. Stock solution of SsnB was prepared in dimethyl sulfoxide (DMSO). Cells treated with different concentrations of SsnB in DMEM with 10% FBS were grown for subsequent days. Cells treated with equal volume of DMSO were used as control.

Cell Viability Assay

The viability of SsnB-treated cells was determined by MTT assay following manufacturer's instructions (Roche diagnostics corporation, Indianapolis, Ind.). Briefly, cells ($1 \times 10^4$ cells/well) grown in 96-well cell culture plate were incubated with or without SsnB in 100 µl of complete culture medium with 10% FBS. After treatments, cells were incubated with 10 µl of MTT reagent for 4 h and then incubated overnight in solubilization buffer (100 µl) at 37° C. Absorbance of the formazan product was read at 575 nm in spectramax spectrophotometer (Molecular Devices, Sunnyvale, Calif.). A reference wavelength of 690 nm was used to detect background. The measured absorption directly correlated with the number of viable cells in culture. The experiments were performed in triplicate and repeated at least three times.

Cell Cycle Analyses by Flow Cytometry

The cell cycle progression was determined by flow cytometer analysis. Neuroblastoma cells were treated with SsnB or DMSO in DMEM with 10% FBS. Cells were collected after trypsinization with trypsin-EDTA solution (Atlanta Biologicals) and washed with 1× phosphate buffered saline (PBS). Approximately $1 \times 10^6$ cells were suspended in 300 µl of ice-cold 1×PBS, fixed by adding 700 µl of chilled absolute ethanol (to make final ethanol concentration 70%) drop wise and incubated for overnight at −20° C. Cells were pelleted at 1000×rpm for 5 min at 4° C., washed with 1×PBS for 3 times and stained with propidium iodide (Sigma-Aldrich, St. Louis, Mo.) by adding 1 ml of propidium iodide staining solution (containing 20 µg/ml propidium iodide and 10 µg/ml DNase-free RNase A in 0.1% Triton X-100/PBS) for 1 h on ice in dark. Samples were subjected to fluorescence-activated cell sorting analyses utilizing Beckman Coulter flow cytometer (Beckman Coulter, Indianapolis, Ind.). A minimum of 10,000 events were analyzed in each experiment.

Immunofluorescence Microscopy

For immunofluorescence staining, cells grown in Lab-TekII chamber slides (Fisher Scientific, Pittsburgh, Pa.) were treated with SsnB in complete culture medium. After treatments, cells were washed with 1×PBS, fixed with 4% paraformaldehyde/PBS for 20 min, and permeabilized with 0.2% Triton X-100/PBS for 10 min at room temperature. Cells were washed with 1×PBS for 3 times and blocked with 5% immunoglobulin (IgG) free-bovine serum albumin (BSA; Jackson ImmunoResearch Laboratories, West Grove, Pa.) in 1×PBS for overnight at 4° C. Cells were incubated with antibody raised against active form of caspase-3 (Cell Signaling Technology, Danvers, Mass.) diluted in 2.5% BSA/PBS for overnight at 4° C. Primary antibodies were detected with secondary antibodies conjugated with fluorescein isothiocyanate (FITC; Santa Cruz Biotechnology, Dallas, Tex.) for 2 h at room temperature. After washing with 1×PBS, cells were mounted with antifade Vectashield mounting media (Vector Laboratories, Burlingame, Calif.), and signals were visualized under Nikon-E600 fluorescence microscope. Nuclei were counterstained with 4',6-diamidino-2-phenylindole (DAPI; Sigma).

Total Cell Protein Isolation and Western Blot Analyses

After treatment with SsnB, cells were collected, washed with 1×PBS, and lysed with 1× cell lysis buffer (Cell Signaling Technology, Danvers, Mass.) containing phenylmethylsulfonyl fluoride (PMSF) and protease inhibitors (aprotinin and leupeptin) for 30 min on ice, and centrifuged at 12000×rpm for 10 min at 4° C. Supernatant (total cell protein) was collected and stored at −80° C. Protein concentration was determined by bicinchoninic acid method using BCA protein assay kit (Pierce/ThermoScientific, Waltham, Mass.). Equal amount of proteins were diluted with 5× Laemmli samples loading buffer and boiled for five minutes. The proteins were subjected to sodium dodecyl sulfate (SDS)-polyacrylamide gel electrophoresis and analyzed by Western blots. Briefly, after electrophoresis, proteins were transferred on polyvinylidene difluoride (PVDF) membrane at 100 volt for 3 h in cold room. Membrane was blocked with 5% non-fat dry milk/TBST (20 mM Tris-Cl, pH 7.4; 150 mM NaCl with 0.1% Tween-20) for 4 h at room temperature followed by incubation in primary antibodies diluted in 2.5% non-fat dry milk/TBST for overnight at 4° C. After washing with TBST, membrane was incubated with secondary antibodies (horseradish peroxidase-conjugated goat anti-rabbit or goat anti-mouse IgG; Santa Cruz Biotechnology, Dallas, Tex.) diluted in 2.5% non-fat dry milk/TBST for 3 h at room temperature. Signals were detected by chemiluminiscence detection kit (Pierce/Thermo Fisher Scientific, Rockford, Ill.). Primary antibodies used were cleaved caspase-3 and β-actin (Cell Signaling Technology), N-myc and p53 (Santa Cruz Biotechnology).

Detection of Reactive Oxygen Species Generation

The production of reactive oxygen species (ROS) in SsnB-treated neuroblastoma cells was detected by a cell-permeable fluorescence probe $H_2DCFDA$ (carboxy-2',7'-dichlorodihydrofluorescein diacetate) according to the manufacturer's instructions (Invitrogen, Carlsbad, Calif.). Briefly, neuroblastoma cells were cultured in DMEM with 10% FBS in Lab-TekII chamber slides (Fisher Scientific, Pittsburg, Pa.) and treated with SsnB for 2 days (SH-SY5Y and IMR-32 cells), 3 days (NGP cell) or 4 days (SKNF-1 and SK-N-BE(2) cells). After treatments, cells were washed with Hank's buffered salt solution (HBSS; Thermo Scientific, Waltham, Mass.) and incubated with 25 µM of carboxy-$H_2DCFDA$ dye for 30 min at 37° C. in dark. Nuclei were counterstained with DAPI. Cells were washed three times with HBSS, mounted with Vectashield mounting medium (Vector Laboratories), and immediately examined under Nikon-E600 fluorescence microscopy equipped with fluorescein isothiocyanate (FITC) filter. Oxidation of $H_2DCFDA$ probe occurs almost exclusively in the cytosol, and generates a fluorescence that is proportional to ROS generation in that cell. As a negative control, cells without $H_2DCFDA$ dye were used to detect autofluorescence. The fluorometric analysis to detect generation of ROS was performed. Briefly, after treatments with SsnB as mentioned above, cells were labeled with carboxy-$H_2DCFDA$ dye (25 µM) for 30 min at 37° C. Cells were trypsinized, washed, and re-suspended in PBS and fluorescence intensity was monitored at excitation wavelength 485 nm and emission wavelength 530 nm with a spectramax spectrophotometer (Molecular Devices, Sunnyvale, Calif.).

Colony Formation Assay

A two layer soft agarose assay system was used in these studies. Approximately 1×10$^4$ cells were suspended in 0.35% agarose in DMEM with 10% FBS, and were gently laid on the bottom agarose layer containing 0.8% agarose with DMEM+10% FBS in 35 mm$^2$ cell culture dishes. Once solidified, the dishes were incubated at 37° C. in a humidified chamber with 5% CO$_2$. Next day, 500 µl of complete cell culture medium with respective concentrations of SsnB was added, and cells were allowed to grow for 45 days in an incubator chamber. Fresh medium with respective concentrations of SsnB was added to the dishes in every 5 days. Cells treated with equal volume of DMSO were used as control. At the end of experiments, cells were stained with 0.1% crystal violet and cell colonies (more than 15 cells per colony) were counted under the light microscope.

Hanging-Drop Assay for Spheroid Formation

3-D in vitro hanging drop assay was carried out to detect the SsnB effect in neuroblastoma spheroid formation. Neuroblastoma cells were prepared as single cell suspension in complete culture medium (DMEM+10% FBS) without or with SsnB (1 and 10 µM). Twenty microliter drops of each prepared cell suspension containing 20,000 cells/drop were pipetted into the inner side of the lid of a 60 mm diameter tissue culture dish. The lid was gently inverted and placed on top of the culture dish filled with 5 ml of sterile 1×PBS to humidify the culture chamber. The drops were incubated under tissue culture conditions (at 37° C. and 5% CO$_2$) allowing the cells to form aggregate at the base of the droplet. The cells in each droplet were photographed using Olympus SZX2 stereo microscope (Olympus America Inc., Center Valley, Pa.).

Measurement of Glutathione (GSH) Level

Cells treated with SsnB or DMSO were washed and re-suspended in PBS and the intracellular GSH level was measured by luminescence based GSH-Glo glutathione assay kit (Promega, Madison, Wis.) following manufacturer's protocol. The luminescence was monitored in a luminometer (Promega Biosystems, Sunnyvale, Calif.).

Data Analysis

Data are presented as the mean and standard deviation (S.D.) of at least three independent experiments. Comparisons were made among the groups using one-way ANOVA followed by Tukey-Kramer ad hoc test (GraphPad software, La Jolla, Calif.). A p-value <0.05 was considered significant.

Results

SsnB Inhibits the Survival of Neuroblastoma Cells

To test the inhibitory effects of SsnB on neuroblastoma cell survival, human neuroblastoma cell lines of different genetic background (SH-SY5Y, SKNF-1, NGP, IMR-32 and SK-N-BE(2) cells) were treated with 1 µM, 5 µM, 10 µM or 20 µM concentration of SsnB under in vitro conditions. Following SsnB treatments, neuroblastoma cell were grown and were photographed under light microscope to evaluate the cell morphology. The phase contrast images as shown in FIG. 1A demonstrated that SsnB alters the cellular appearance and promotes cell death (as evaluated by cell morphology; round and clumping of cells is indication of cell death) in all of these neuroblastoma cell lines. SsnB at 10 µM and above concentrations changed the morphology (as evaluated by rounded cells and indication of cell death) of SH-SY5Y cells and IMR-32 cells (after 2 days treatment), NGP (after 3 days treatment), SKNF-1 and SK-N-BE(2) cells (after 4 days treatment) compared to control DMSO-treated cells. However, such morphological changes were not significant at 1 or 5 µM concentration of SsnB in any cell line tested.

Figure 1B:
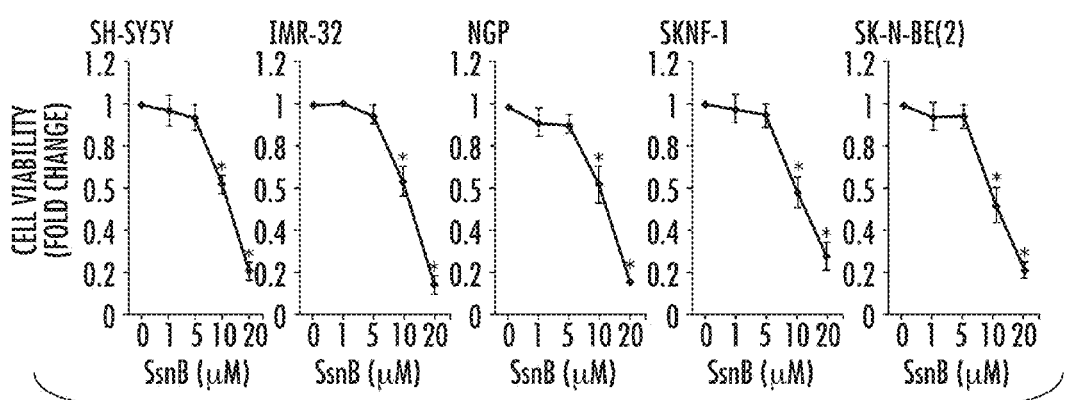
FIG. 1B illustrates bar diagrams showing cell viability after SsnB treatment as evaluated by MTT assays. Neuroblastoma cells were treated with SsnB (1, 5, 10, or 20 $\mu M$) for 2 days (SH-SY5Y and IMR-32), 3 days (NGP) or 4 days (SKNF-1 and SK-N-BE(2) cells) and cell viability was measured by MTT assay at 575 nm. Data are represented in fold change and *$p<0.05$ vs control.

MTT assay was carried out to examine the effects of SsnB on viability of all the above listed neuroblastoma cells. After 2 days (SH-SY5Y and IMR-32), 3 days (NGP cells) or 4 days (SKNF-1 and SK-N-BE(2) cells) treatment with SsnB (1, 5, 10 and 20 µM), MTT cell viability assays were performed. The bar diagram in FIG. 1B shows that SsnB inhibited, effectively and dose-dependently, the viability of all neuroblastoma cell lines tested. Compared to DMSO, SsnB at and above 10 µM concentration significantly reduced the viability of these cell lines (*p<0.05 vs DMSO) and the IC20 and IC50 were found to be in the range of 6-8 µM and 10-12 µM, respectively. No significant difference in cell survival was observed at SsnB at 1 µM or 5 µM concentrations compared to control DMSO-treated neuroblastoma cells (p>0.05 vs DMSO). No cytotoxic response of SsnB at these concentrations (and up to about 100 µM) was observed in various normal human cells e.g. human monocytic THP-1 cells, phorbol 12-myristate 13-acetate-differentiated THP-1 macrophages, human umbilical vein endothelial cells and human aortic smooth muscle cells. These data demonstrate the anti-proliferative activity of SsnB on human neuroblastoma cells, and suggest that SH-SY5Y and IMR-32 cells were most sensitive, NGP cell was moderately sensitive, SKNF-1 and SK-N-BE(2) cell lines were least sensitive towards SsnB treatment. Since 50% cell viability was observed in range of 10-12 µM SsnB conc., we used 10 µM as higher conc. and 1 µM lower conc. in our further experiments.

SsnB Regulates Cell Cycle Progression in Neuroblastoma Cells

Figure 1C:
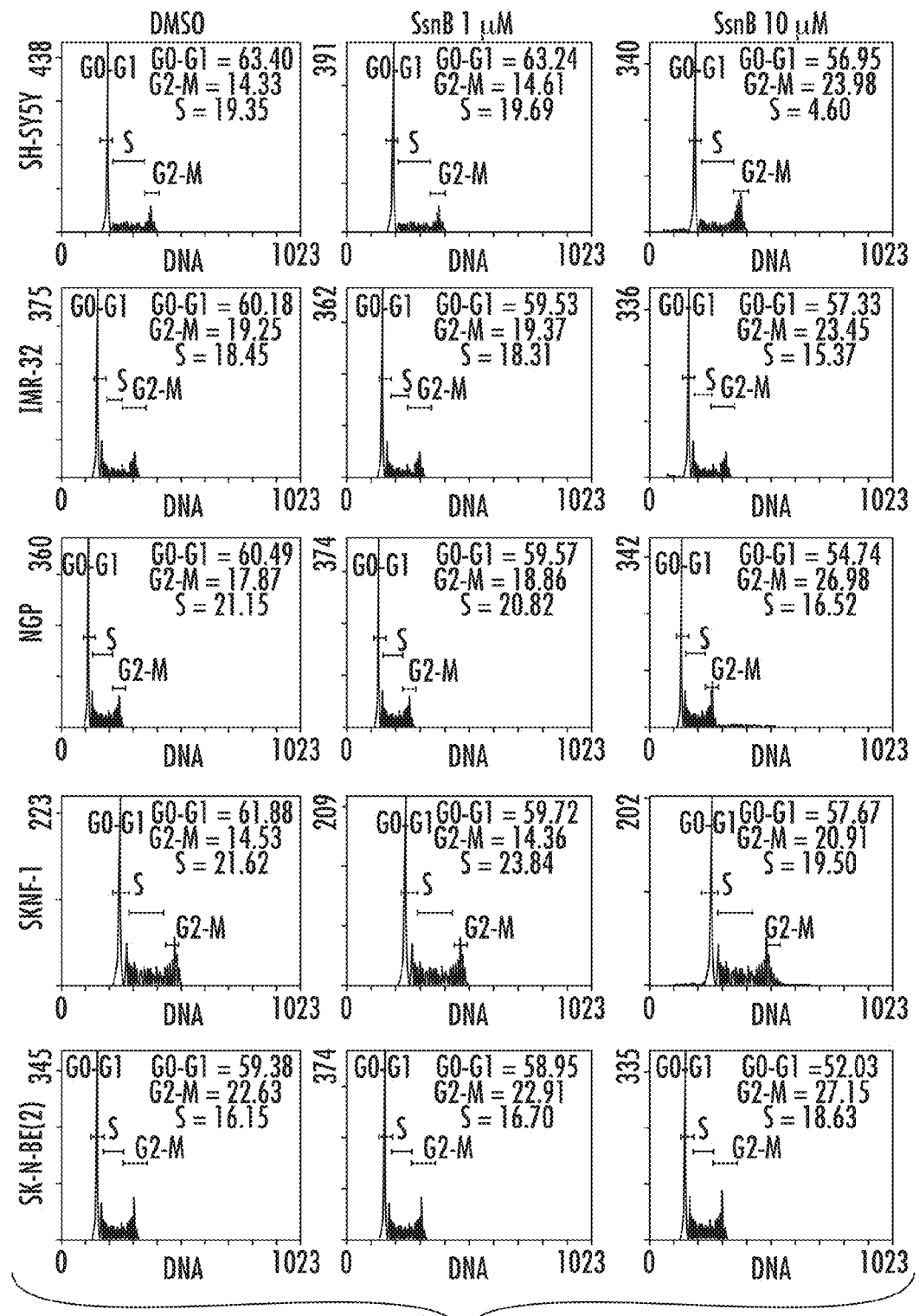
FIG. 1C illustrates the SsnB arrest cell cycle at G2/M phase. The representative histograms illustrate the cell cycle progression of neuroblastoma cells in the presence of SsnB. Neuroblastoma cells were labeled with propidium iodide and cell cycle stage was analyzed by flow cytometry.

To test whether SsnB-induced cell growth inhibition occurs through cell cycle arrest, cell cycle distribution was analyzed by flow cytometry after DNA staining with propidium iodide. Representative histogram in FIG. 1C showed that 2 days (SH-SY5Y, IMR-32) or 3 days (NGP cells) exposure of SsnB (10 µM) resulted in increase of G2-M phase cells when compared with DMSO-treated controls (G2/M for SH-SY5Y, SsnB 10 µM=23.98% vs control=14.33%; for IMR-32, SsnB 10 µM=23.45% vs. control=19.25%; and for NGP, SsnB 10 µM=26.98% vs control=17.87%). Similarly, SsnB treatment for 4 days increases the number of SK-N-BE(2) cells and SKNF-1 cells in G2/M phase, compared to control (G2/M for SKNF-1, SsnB 10 µM=20.91% vs. control=14.53%; for SK-N-BE(2) cells, SsnB 10 µM=27.15% vs. control=22.63%). The SsnB (10 µM) induced increase in G2/M fraction was accompanied by a decrease in G0/G1 phase cells. SsnB at 1 µM concentration did not affect cell cycle progression compared to DMSO-treated controls. These results indicated that the exhibited anti-proliferative effect of SsnB (10 µM) may be exerted by cell cycle arrest at G2-M transition in these neuroblastoma cell lines.

SsnB Generates Reactive Oxygen Species (ROS) in Neuroblastoma Cells

Figure 2A:
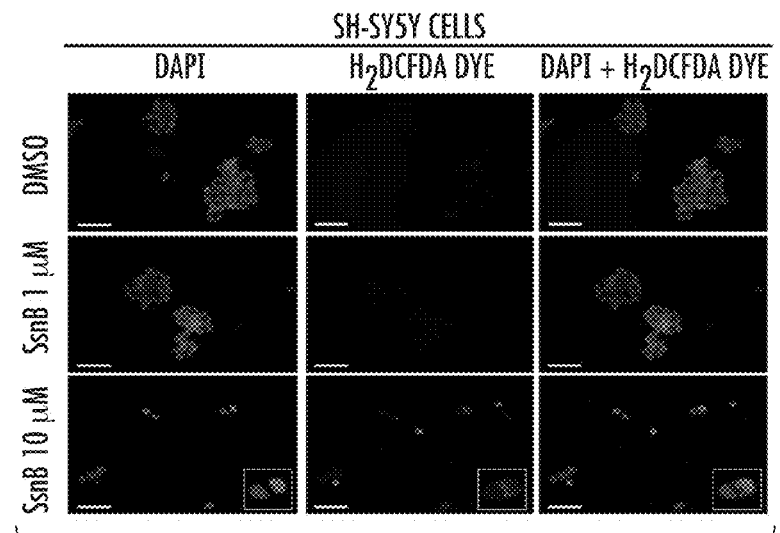
FIG. 2A presents results of reactive oxygen species (ROS) generation by cells by use of $H_2DCFDA$ staining after DMSO or SsnB treatments (1 $\mu M$ or 10 $\mu M$) for 2 days (SH-SY5Y cells). Signals were examined under fluorescence microscope. Images are representative of at least three independent experiments. Scale bar=100 $\mu m$.
Figure 2B:
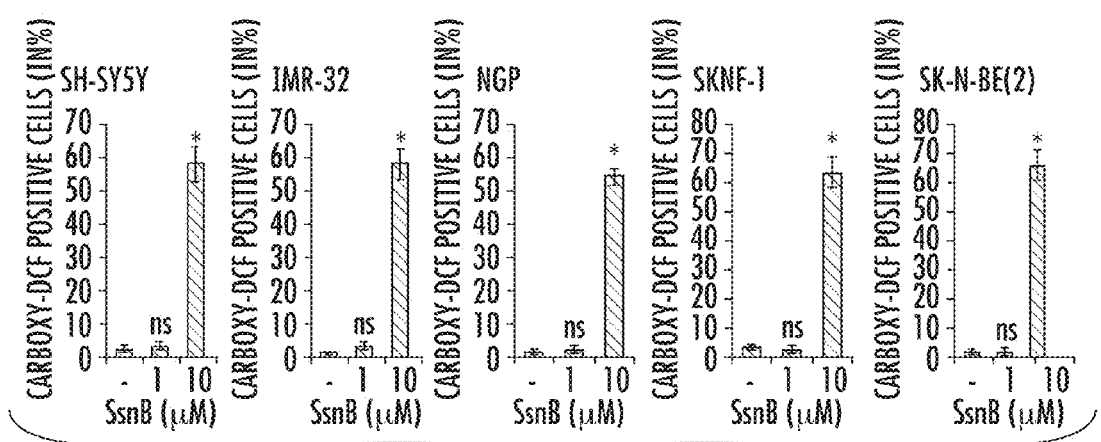
FIG. 2B illustrates the results of quantification of the carboxy-DCF positive cells by ImageJ programme. Cells were treated with or without SsnB (1 $\mu M$ or 10 $\mu M$) in complete culture medium (Dulbecco's Modified Eagle's Medium, DMEM, supplemented with 10% fetal bovine serum, FBS) for 2 days (SH-SY5Y and IMR-32), 3 days (NGP) or 4 days (SKNF-1 and SK-N-BE(2) cells).

To test whether SsnB-induced cell death resulted from increased level of ROS, H$_2$DCFDA staining was performed. H$_2$DCFDA is a cell-permeable non-fluorescent indicator for ROS that is oxidized in the presence of reactive oxygen species to fluorescent molecule carboxy-DCF. Neuroblastoma cells treated with SsnB for 2 days (SH-SY5Y and IMR-32), 3 days (NGP cells) or 4 days (SKNF-1 and SK-N-BE(2) cells) were labeled with H$_2$DCFDA dye for 30 min and cells were immediately examined under fluorescence microscopy. The carboxy-DCF positive cells were quantitated by imageJ software and plotted. The representative fluorescence images of SH-SY5Y cells in FIG. 2A indicated that the number of carboxy-DCF positive cells was significantly increased at 10 µM concentration of SsnB compared to DMSO-treated samples (*p<0.05 vs DMSO;

FIG. 2B). The ROS generation was observed exclusively in those SsnB treated cells which contain fragmented nuclei. Representative fluorescence images from SH-SY5Y cells showed that compared to DMSO and SsnB (1 µM), SsnB at 10 µM induced ROS generation ($H_2$DCFDA-positive cells) and signals were exclusively present in cytoplasm (as shown in enlarged single and merged images, FIG. 2A). Nuclei were counterstained with DAPI. Similar to SH-SY5Y cells, SsnB (10 µM) significantly increased carboxy-DCF positive cells in other neuroblastoma cell lines tested (FIG. 2B; *$p<0.05$ vs DMSO). In negative control, no such staining was observed in cells processed without $H_2$DCFDA dye ruling out the autofluorescence (data not shown). These results suggest that SsnB promotes intracellular ROS production in neuroblastoma cell lines.

Figure 2C:
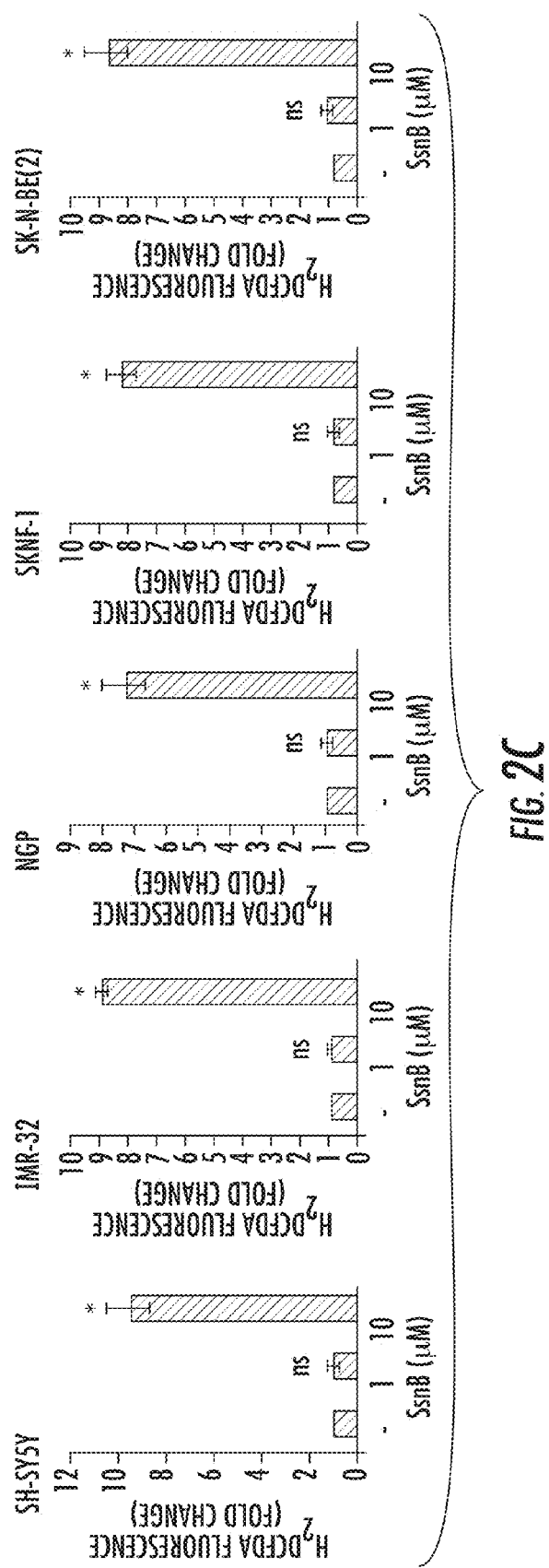
FIG. 2C presents bar diagrams representing the fold change in fluorescence intensity of $H_2DCFDA$ in cells treated with or without SsnB (1 μM or 10 μM) for 2 days (SH-SY5Y and IMR-32), 3 days (NGP) or 4 days (SKNF-1 and SK-N-BE(2) cells). After labeling with $H_2DCFDA$ dye (25 μM) for 30 min fluorescence intensity was monitored at excitation wavelength 485 nm and emission wavelength 530 nm. Values are mean and S.D. of three experiments. *$p<0.05$, SsnB 10 μM vs control; ns=nonsignificant vs control.

SsnB-induced generation of ROS was also evaluated by fluorometry assay. Neuroblastoma cells as treated above were incubated with $H_2$DCFDA dye for 30 min and the fluorescence intensity was measured at 485 nm (excitation wavelength) and 530 nm (emission wavelength). The $H_2$DCFDA fluorescence intensity (as measure of generation of ROS) was significantly increased in cells treated with SsnB (10 µM) compared to DMSO control (*$p<0.05$, SsnB 10 µM vs DMSO; FIG. 2C) whereas the $H_2$DCFDA fluorescence intensity levels were almost similar in SsnB (1 µM) and DMSO-treated cells (ns=nonsignificant, SsnB 1 µM vs DMSO; FIG. 2C).

Figure 2D:
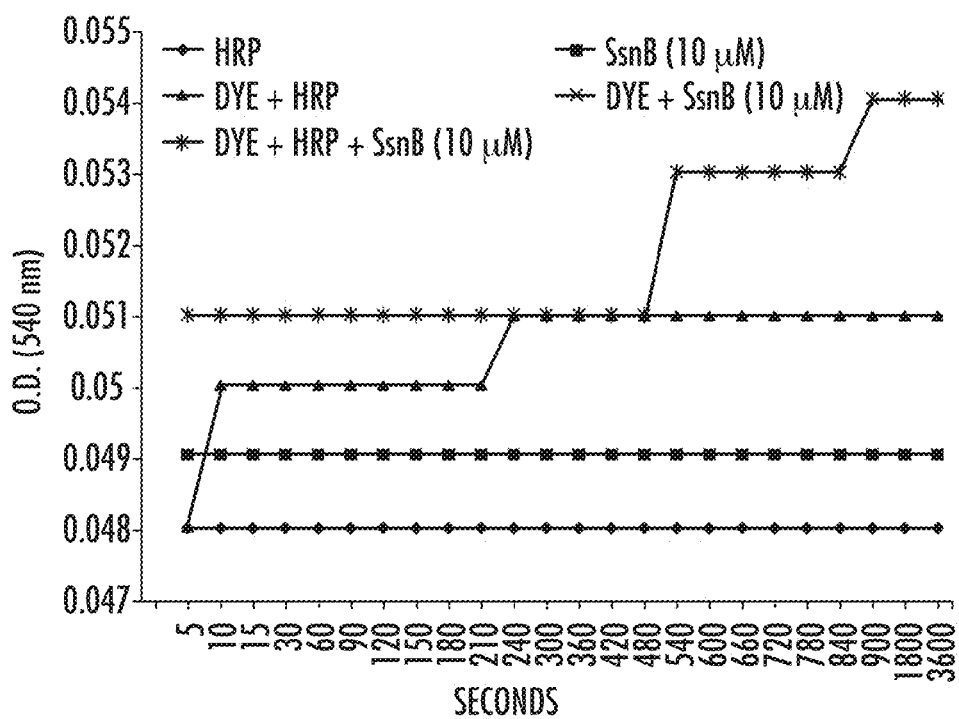
FIG. 2D and FIG. 2E illustrate the ROS generating capacity of SsnB evaluated in a cell-free system containing $H_2DCFDA$ (25 μM), horseradish peroxidase (HRP, 5 units/ml), SsnB (10 μM) and glutathione (GSH, 0.25 or 2.5 μM) alone or in various combinations. Optical density (O.D.) at 540 nm were taken at different time points and plotted.
Figure 2E:
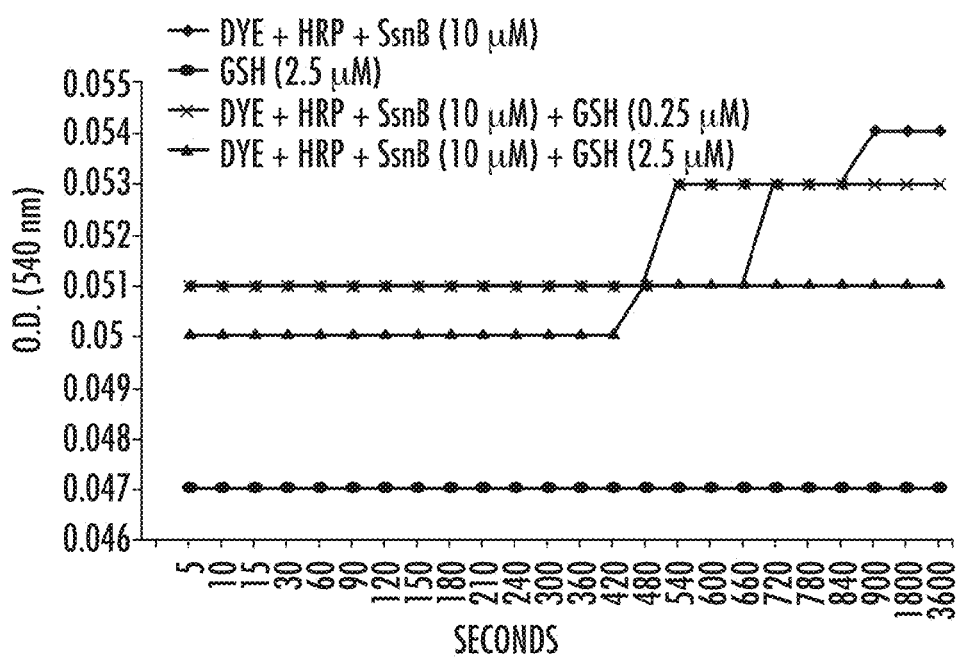

In a reaction system, after the removal of acetate group by cellular esterases and oxidation by reactive oxygen species, the non-fluorescent carboxy-$H_2$DCFDA dye is oxidized to fluorescent molecule carboxy-DCF. To measure the ROS-generating activity of SsnB, the oxidation of carboxy-$H_2$DCFDA dye was monitored in a cell-free system containing carboxy-$H_2$DCFDA dye, horseradish peroxidase (HRP) and SsnB at 540 nm. HRP was used to supply esterase since without esterase carboxy-$H_2$DCFDA is not sensitive to oxidant. As shown in FIG. 2D, the optical density (OD) value of reaction containing SsnB (10 µM)+$H_2$DCFDA dye (25 µM) remained constant throughout the experiment suggesting that SsnB (10 µM) alone was not able to oxidize $H_2$DCFDA to the fluorescent compound carboxy-DCF. After addition of HRP (5 units/ml) in the reaction mixture containing SsnB (10 µM)+$H_2$DCFDA dye (25 µM), the OD value increased by 2% in the first 240 sec and further increased by 8% after 15 min compared to $H_2$DCFDA+HRP reaction, indicating the increased oxidation of $H_2$DCFDA to the fluorescent compound. These results suggest that in the presence of cellular peroxidases SsnB oxidizes non-fluorescent $H_2$DCFDA dye into the fluorescent compound. Addition of GSH (0.25 µM or 2.5 µM) in a reaction containing SsnB (10 µM)+$H_2$DCFDA dye (25 µM)+HRP (5 units/ml) lowers the OD value in a dose dependent manner indicating that GSH as an antioxidant removes the free radicals generated by SsnB in reaction mixture which in turn inhibits the oxidation $H_2$DCFDA dye (FIG. 2E).

Figure 2F:
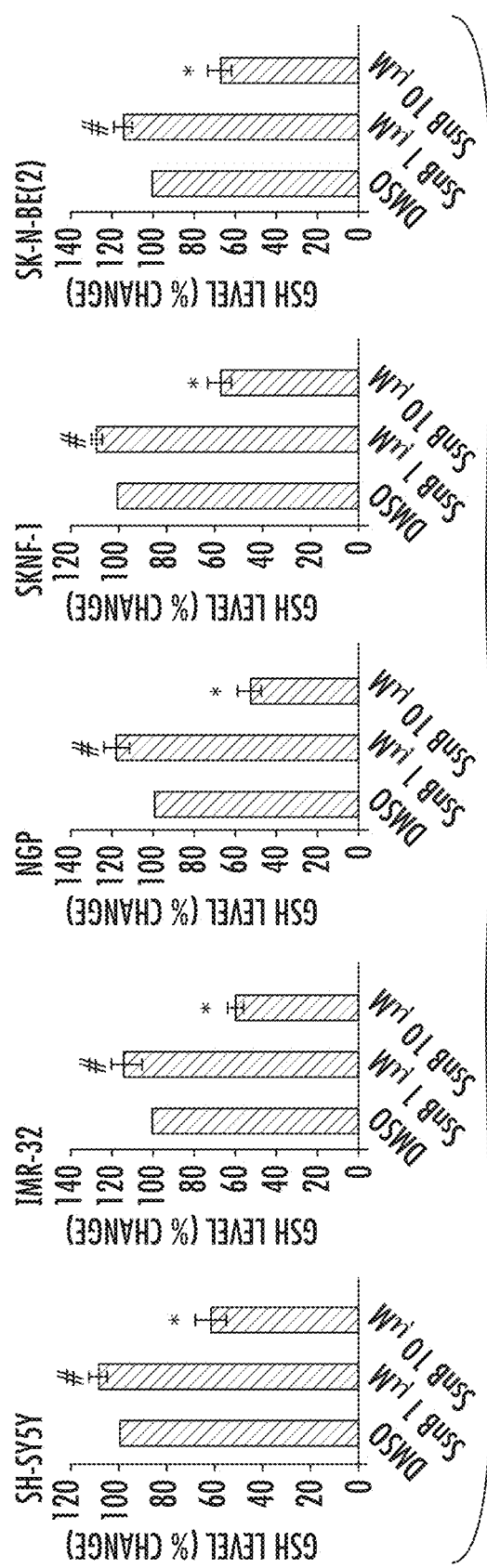
FIG. 2F presents the cellular glutathione (GSH) level of neuroblastoma cells treated with SsnB at 1 μm or 10 μm or with DMSO for 2 days (SH-SY5Y, IMR-32), 3 days (NGP) or 4 days (SKNF-1 and SK-N-BE(2)) using luminescence based glutathione assay kit. Values were expressed in % change compared to control samples (considering control as 100%) and plotted. Bar represents mean and S.D. of three independent experiments and *$p<0.05$, SsnB 10 μM vs control; #$p≤0.05$, SsnB 1 μM vs control.

At the cellular level, reduced glutathione (GSH) protects cells from oxidative damage resulted from increased superoxides, peroxides and free radicals. Since SsnB induces oxidative stress, SsnB affect of intracellular levels of GSH in neuroblastoma cells was examined. After treatment with SsnB for 2 days (SH-SY5Y and IMR-32), 3 days (NGP cells) or 4 days (SKNF-1 and SK-N-BE(2) cells), the cellular GSH level was measured by luminescence based glutathione assay kit. Compared to control, the GSH level was significantly decreased (~40% of control) in cells treated with 10 µM SsnB (*$p<0.05$, SsnB 10 µM vs control; FIG. 2F). However, the level of GSH at 1 µM SsnB concentration was slightly higher or equal to control levels (#$p\leq0.05$ vs control) suggest that at initial stage basal antioxidant mechanism trying to protect the cell against the toxic effects of SsnB. These results indicated that the GSH depletion was unable to protect neuroblastoma cells against SsnB (10 µM)-induced increased oxidative stress.

SsnB Promotes DNA Fragmentation in Neuroblastoma Cells

Figure 3A:
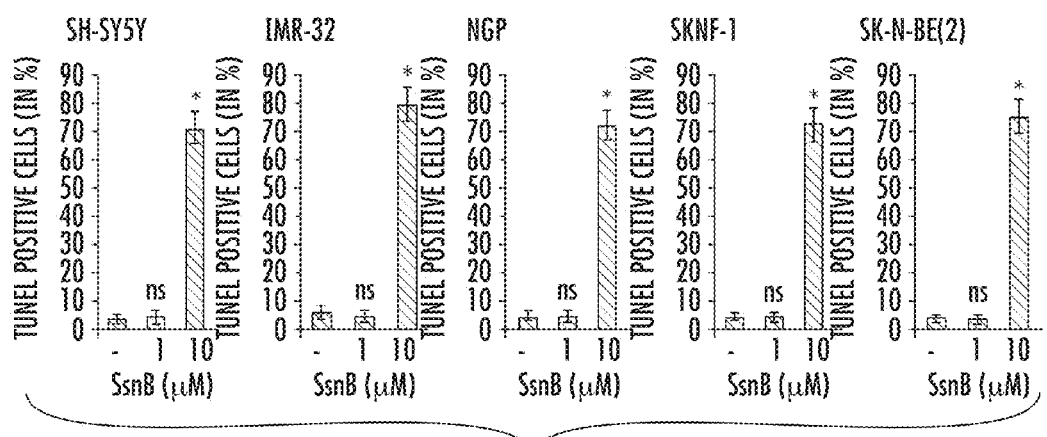
FIG. 3A graphically presents the DNA fragmentation of SsnB-treated neuroblastoma cells (SH-SY5Y and IMR-32 for 2 days, NGP for 3 days, and SKNF-1 and SK-N-BE(2) cells for 4 days) at either 1 μm or 10 μm or with DMSO by TUNEL assay. The number of TUNEL-positive cells (indicator of DNA fragmentation) were counted by ImageJ programme and plotted. The bar represents mean and S.D. of three independent experiments and *$p<0.05$ vs control. ns=nonsignificant vs control.
Figure 3B:
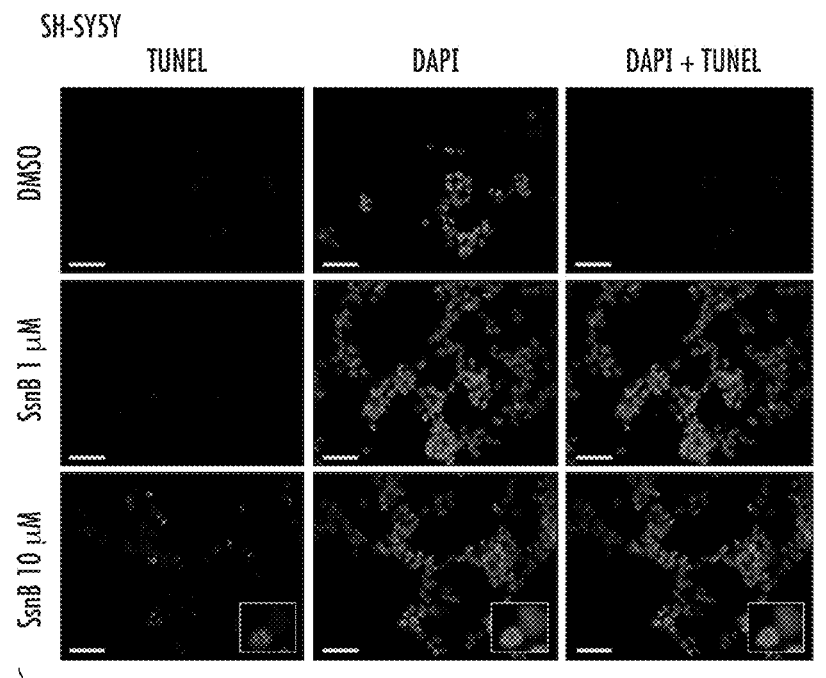
FIG. 3B includes representative images from SH-SY5Y TUNEL-assay showing that the number of TUNEL-positive cells (as indicator of DNA fragmentation) were more in SsnB-treated groups (10 μM) compared to DMSO or SsnB (1 μM)-treated group. The enlarged overlapped and individual images showing cells with a typical apoptotic nucleus as stained with DAPI, TUNEL, or a combination thereof is observed in those cells which had fragmented nuclei. Scale bar=100 μm.

Increased levels of ROS are known to induce oxidative stress which in turn cleaves DNA that leads to cell death. SsnB-induced DNA fragmentation in neuroblastoma cells was examined by terminal deoxynucleotidyl transferase dUTP nick end labeling (TUNEL) assay. In this assay, nicked DNA is identified by the addition of fluorophore-labeled dUTPs by enzyme terminal deoxynucleotidyl transferase (TdT) to the terminal ends of damaged DNA in apoptotic cells. The TUNEL-positive cells were quantitated by ImageJ programme and plotted. The number of TUNEL-positive cells at 10 µM concentration of SsnB were significantly higher in all neuroblastoma cells compared to control (*$p<0.005$ vs control; FIG. 3A). The TUNEL-positive cells in SsnB (1 µM) were almost similar to DMSO-treated samples (ns=nonsignificant vs control, $p>0.05$). The representative fluorescence images from SH-SY5Y cells as shown in FIG. 3B indicated that SsnB at 10 µM concentration induced DNA fragmentation, and the staining for fragmented DNA (TUNEL-positive staining) and nuclei were overlapped in a single cell (as shown in enlarged image) suggest that SsnB promotes apoptosis in these cells. However, such TUNEL-positive cells were not detected in DMSO- or SsnB (1 µM)-treated cells.

SsnB Activates Caspase-3 in Neuroblastoma Cells

Figure 3C:
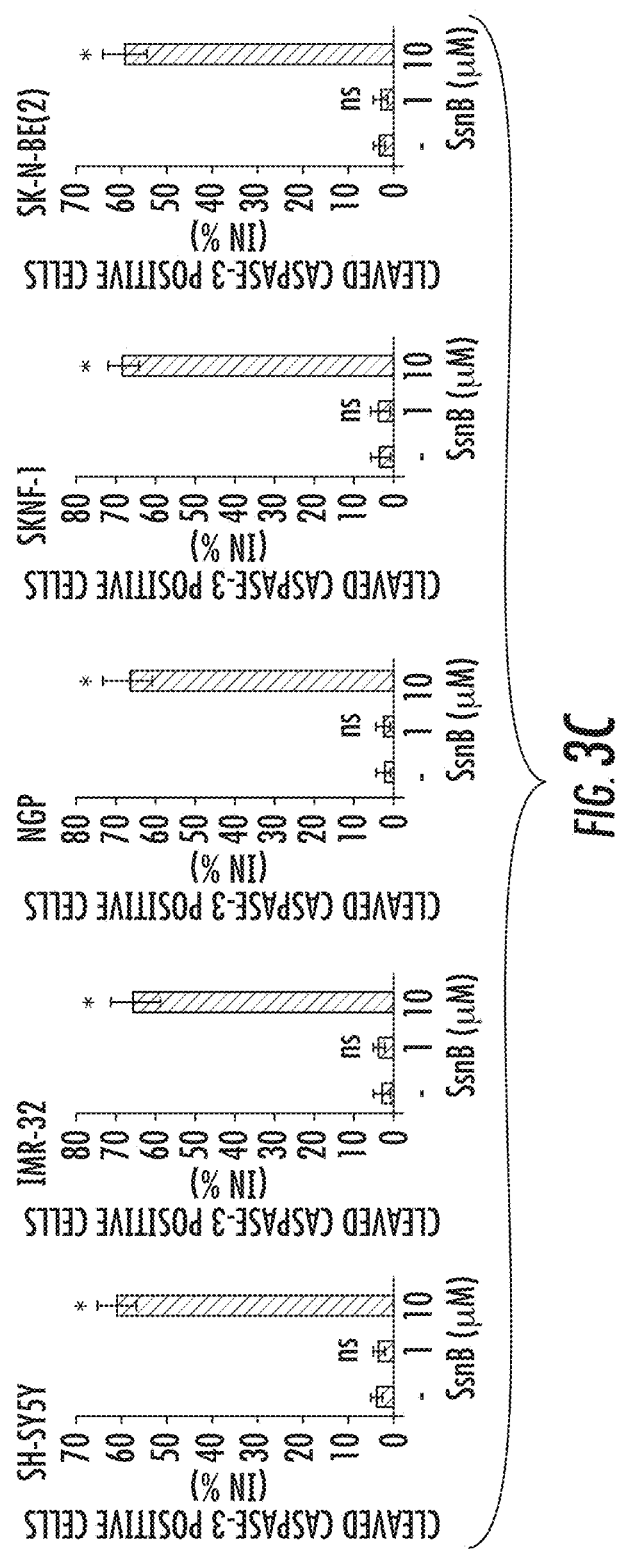
FIG. 3C graphically presents the percentage of DMSO or SsnB-treated neuroblastoma cells (SH-SY5Y and IMR-32 for 2 days, NGP for 3 days, and SKNF-1 and SK-N-BE(2) cells for 4 days) cleaved by caspase-3 following treatment at the given time at either 1 μm or 10 μm. The number of cleaved caspase-3 positive cells were counted by ImageJ programme and plotted. The bar represents mean and S.D. of three independent experiments and *$p<0.05$ vs control. ns=nonsignificant vs control.
Figure 3D:
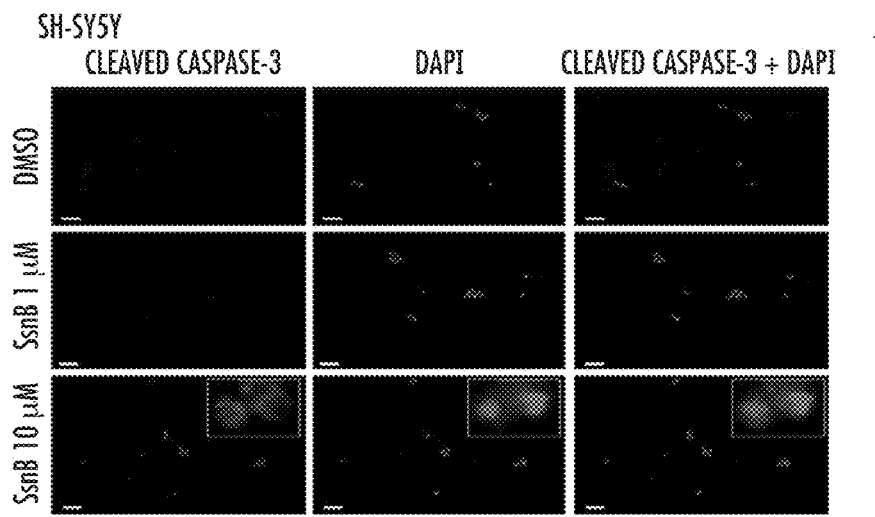
FIG. 3D includes representative immunofluorescence images showing staining for cleaved caspase-3 in SH-SY5Y cells. Enlarged single and overlapped images showing that cleaved caspase-3 staining is exclusively present in the cytoplasm. Scale bar=100 μm.
Figure 3E:
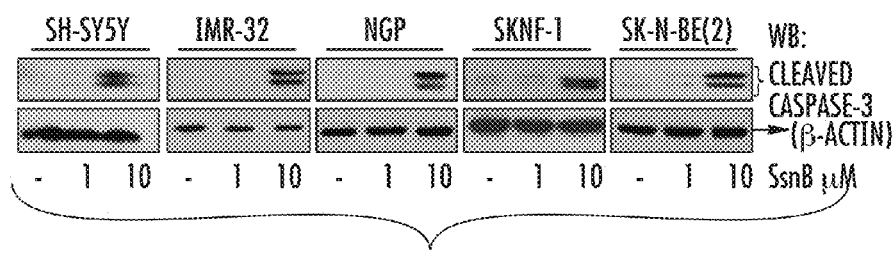
FIG. 3E presents cleaved caspase-3 protein level in DMSO or SsnB-treated neuroblastoma cells as evaluated by Western blotting. Total cell extracts prepared from neuroblastoma cells treated with SsnB (1 μM or 10 μM) or without SsnB were separated on 14% SDS-polyacrylamide gel and Western blotted with cleaved caspase-3 antibody. β-actin was used to check loading differences. Protein signal intensities were calculated form ImageJ programme and the ratios of cleaved caspase-3/β-actin were plotted.
Figure 3F:
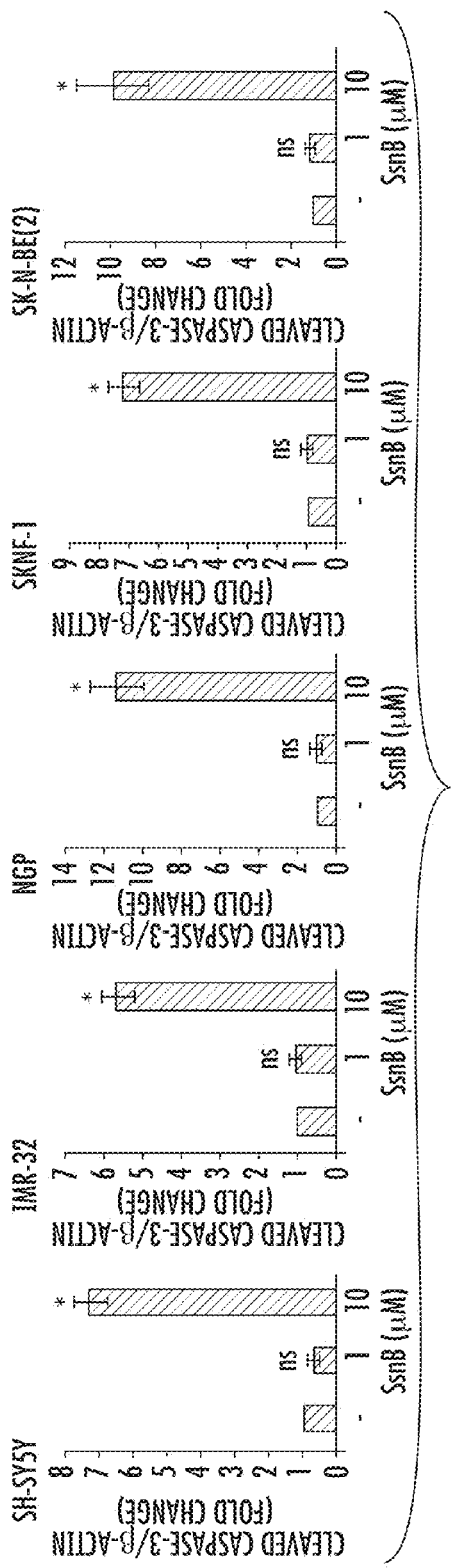
FIG. 3F presents the fold change for the cleaved caspase-3/β-actin in control and SsnB-treated cells at the different treatment levels. Bar represents mean and S.D. of three independent experiments and *$p<0.05$, SsnB 10 μM vs control; ns=nonsignificant vs control.
Figure 3G:
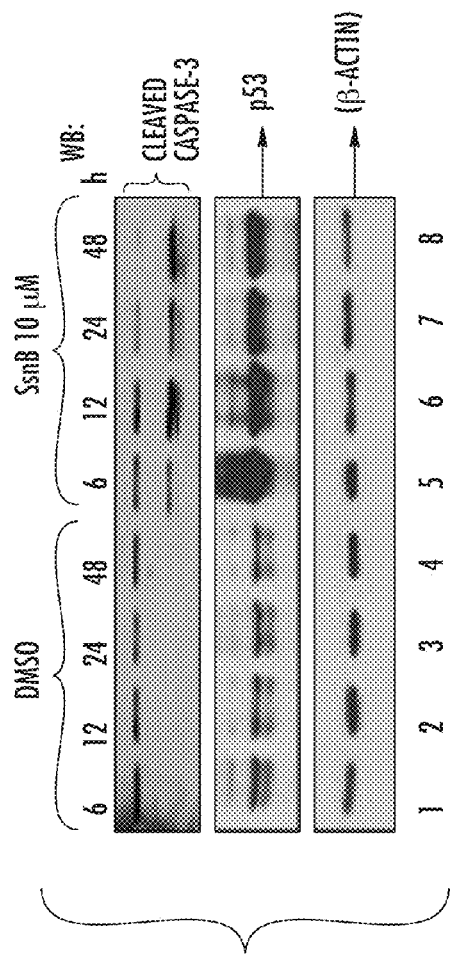
FIG. 3G provides Western blots showing protein expression level for cleaved caspase-3 and p53 in total SH-SY5Y cell extract prepared from DMSO or SsnB treatment (10 μM) at different time points (6, 12, 24, 48 h). β-actin was used to check loading differences.

At cellular level, mitochondria- or receptor (Fas/FasL)-mediated pathways activate caspase signaling cascade which in turn induces DNA damage and initiates programmed cell death (apoptosis). To determine whether SsnB-induced cell death is mediated by caspase activation, Western blotting as well as immunofluorescence assay were performed to detect the active form of caspase-3 in neuroblastoma cells treated with SsnB for 2 days (SH-SY5Y and IMR-32 cells), 3 days (NGP cells) or 4 days (SKNF-1 and SK-N-BE(2) cells). The number of cleaved caspase-3 positive cells were quantitated by ImageJ programme and plotted. The bar diagrams in FIG. 3C demonstrated that SsnB at 10 µM significantly increased the cleaved caspase-3 positive cells compared to DMSO or SsnB (1 µM) treated neuroblastoma cells (*$p<0.005$, SsnB 10 µM vs control). The representative immunofluorescence images for SH-SY5Y in FIG. 3D indicated that the color intensity of cleaved caspase-3 was significantly increased in SsnB-treated (10 µM) cells and the cleaved caspase-3 fluorescence signals were exclusively present in cytoplasm and did not overlap with nucleus (blue). The corresponding Western blots in FIG. 3E demonstrated that the cleaved and active form of caspase-3 protein bands (17 and 19 kDa) were present in protein samples prepared from 10 µM SsnB treated cells (*$p<0.005$, SsnB 10 µM vs control, FIG. 3E and FIG. 3F), while proteins samples from DMSO and SsnB (1 µM) had almost undetectable levels of cleaved caspase-3 (ns=nonsignificant, SsnB 1 µM vs control; FIG. 3E and FIG. 3F). The activation of caspase-3 by SsnB (10 µM) was further examined at different time points (6, 12, 24 and 48 h) in SH-SY5Y cells. The presence of an active form of caspase-3 protein band (~19 kDa) showed that SsnB induced cleavage of caspase-3 in these cells even as early as 6 h SsnB exposure (FIG. 3G, upper panel). Thus, these data suggest that SsnB induces apoptosis through activation of caspase-3 in all neuroblastoma cell lines tested. Increased expression of p53 in SsnB (10 µM) treated cells was also observed as compared to DMSO-treated cells (middle panel; FIG. 3G). Activation of p53, a tumor suppressor protein, leads to growth arrest at G1 or G2 phase of cell cycle, hence, increased expression of p53 by SsnB suggested that p53 might also involve in SsnB-induced cytotoxicity in p53-containing neuroblastoma cells.

SsnB Reduces Expression of N-Myc in Neuroblastoma Cells

Figure 4A:
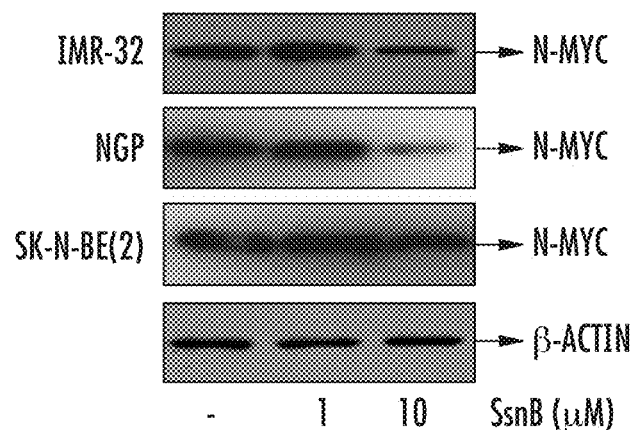
FIG. 4A and FIG. 4B illustrates the N-myc protein level in IMR-32, NGP and SK-N-BE(2) cells.
Figure 4B:
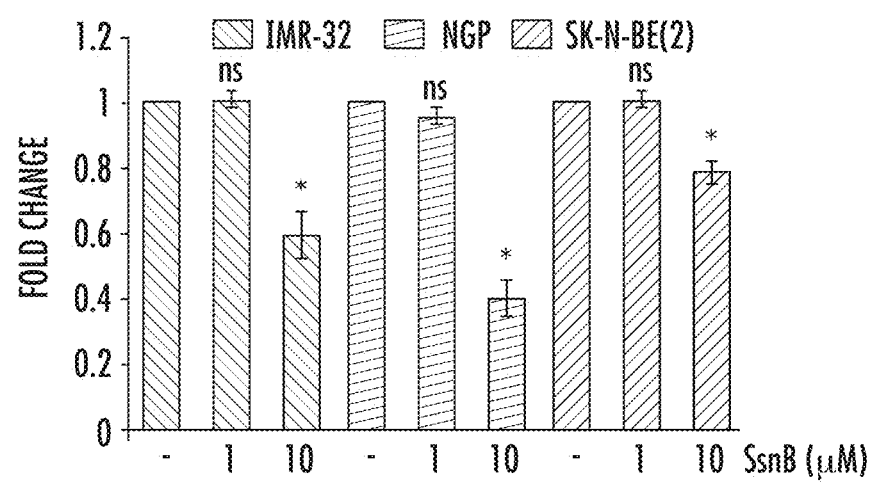

The level of N-myc proteins was evaluated from 2 days (IMR-32), 3 days (NGP cells) or 4 days (SK-N-BE(2) cells) SsnB-treated N-myc amplified neuroblastoma cells by Western blotting, and protein signal intensity was measured by ImageJ programme and plotted. Western blot in FIG. 4A demonstrates that SsnB at 10 µM concentration inhibited the expression of N-myc protein in these cell lines (*p<0.005, SsnB 10 µM vs control; FIG. 4A and FIG. 4B). However such reduction in protein expression was not observed at 1 µM concentration of SsnB (ns=nonsignificant, SsnB 1 µM vs control; FIG. 4A and FIG. 4B).

NAC Attenuates the Inhibitory Effects of SsnB in Neuroblastoma Cells

Figure 5A:
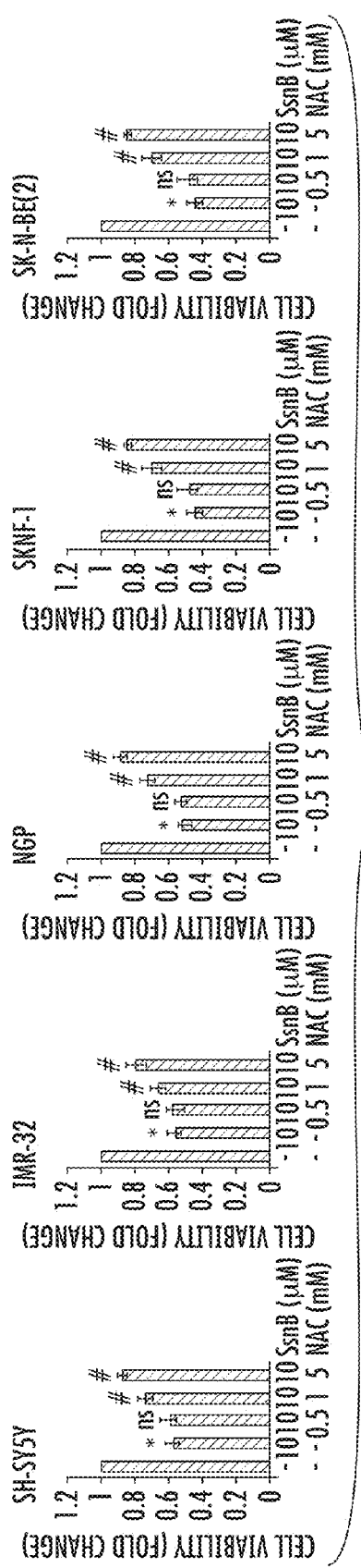
FIG. 5A graphically illustrates the cell viability of neuroblastoma cells following pretreatment with N-acetylcystamine (0.5, 1 or 5 mM) for 1 h followed by SsnB (10 μM) treatment for 2 days (SH-SY5Y and IMR-32), 3 days (NGP) or 4 days (SKNF-1 and SK-N-BE(2) cells). N-acetylcystamine (NAC) is a glutathione (GSH) precursor and acts as an antioxidant. After these treatments MTT cell viability assays were carried out. Bar represents mean and S.D. of three independent experiments and *$p<0.05$ vs control; ns=nonsignificant vs SsnB 10 μM; #$p<0.05$ vs SsnB 10 μM.

The reduced cell viability, increased ROS and decreased GSH levels by SsnB indicated that depletion of glutathione may be a primary cause for the cell death. Addition of N-acetylcystamine (NAC), a GSH precursor and an antioxidant, was examined to determine if NAC can protect neuroblastoma cells from SsnB-induced cell death. To test this hypothesis, neuroblastoma cells were pretreated with NAC (0.5, 1 and 5 mM) for 1 h followed by treatment with SsnB (10 µM) for 2 days (SH-SY5Y and IMR-32 cells), 3 days (NGP cells) or 4 days (SKNF-1 and SK-N-BE(2) cells), and cell viability was measured by MTT assay. MTT cell viability assays showed that NAC treatment suppressed SsnB-induced cell death in a concentration dependent manner (FIG. 5A). SsnB (10 µM) induced neuroblastoma cell death in range of 40-60% (*p<0.05 vs control) whereas presence of NAC (1 mM or 5 mM) significantly increased the viability of SsnB-treated cells (#p<0.05, SsnB 10 µM alone vs. SsnB 10 µM+NAC 1 or 5 mM).

Figure 5B:
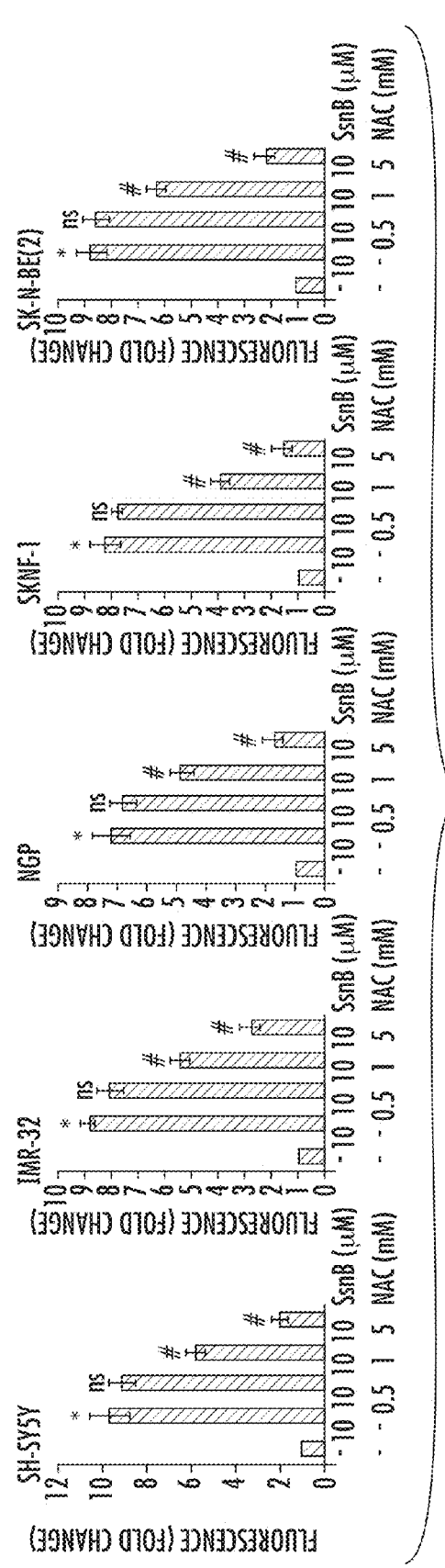
FIG. 5B is a bar diagram representing the fold change in $H_2DCFDA$-fluorescence intensity in cells treated with SsnB (10 μM) alone or in combinations with NAC (0.5, 1 or 5 mM) as described for FIG. 5A. After labeling with $H_2DCFDA$ dye (25 μM) for 30 min fluorescence intensity was monitored at excitation wavelength 485 nm and emission wavelength 530 nm. Bar represents mean and S.D. of three independent experiments and *$p<0.05$ vs control; ns=nonsignificant vs SsnB 10 μM; #$p<0.05$ vs SsnB 10 μM.

The levels of ROS in SsnB-treated cells preincubated with NAC were then measured by fluorometry assay using $H_2DCFDA$ dye. NAC at 1 and 5 mM concentration significantly reduced ROS levels in SsnB (10 µM) treated neuroblastoma cells (#p<0.05, SsnB 10 µM alone vs SsnB 10 µM+NAC 1 or 5 mM; FIG. 5B). These data suggest that NAC as an ROS scavenger removes SsnB-induced generation of ROS in cells.

Figure 5C:
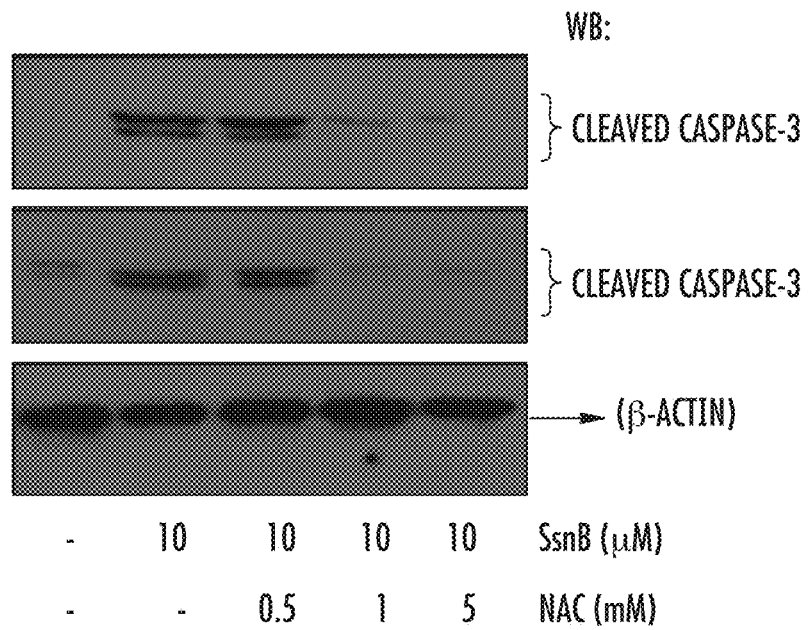
FIG. 5C includes representative Western blots demonstrating the level of cleaved caspase-3 in total cell protein isolated from SH-SY5Y (upper panel) and SK-N-BE(2) cells (middle panel) treated with NAC (0.5, 1 or 5 mM) and SsnB (10 μM) alone or in combinations for 2 days and 4 days, respectively. β-actin was used to check loading differences (lower panel).
Figure 5D:
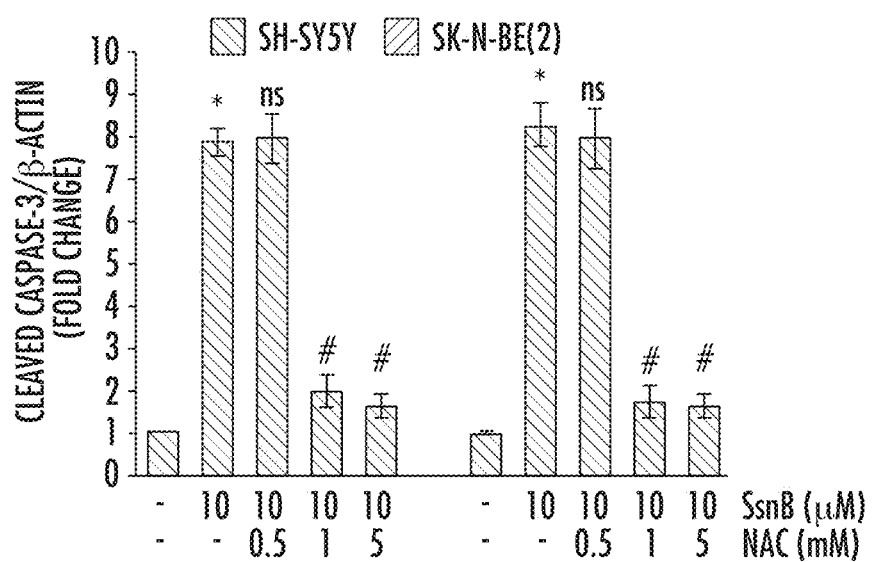
FIG. 5D is a bar diagram representing the ratio of cleaved caspase-3/β-actin protein levels (in fold change) as measured by imageJ programme for the cells of FIG. 5C. The bar represents mean and S.D. of three independent experiments and *$p<0.05$, SsnB 10 μM vs control; ns=nonsignificant vs. control; #$p<0.05$ vs SsnB 10 μM.

Cleaved caspase-3 level in SH-SY5Y cells (2 days treatment) and SK-N-BE(2) cells (4 days treatment) incubated with SsnB (10 µM) with or without NAC (0.5, 1 or 5 mM) was examined by Western blotting. Representative blot in FIG. 5C and corresponding bar diagram (FIG. 5D) demonstrated that pretreatment of NAC (1 and 5 mM) to SsnB treated cells inhibited the activation of caspase-3 and brought to control levels in both SH-SY5Y (upper panel) and SK-N-BE(2) cells (middle panel) (#p<0.05, SsnB 10 µM vs SsnB 10 µM+NAC 1 or 5 mM).

SsnB Reduces the Tumorigenicity of Neuroblastoma Cells

Figure 6A:
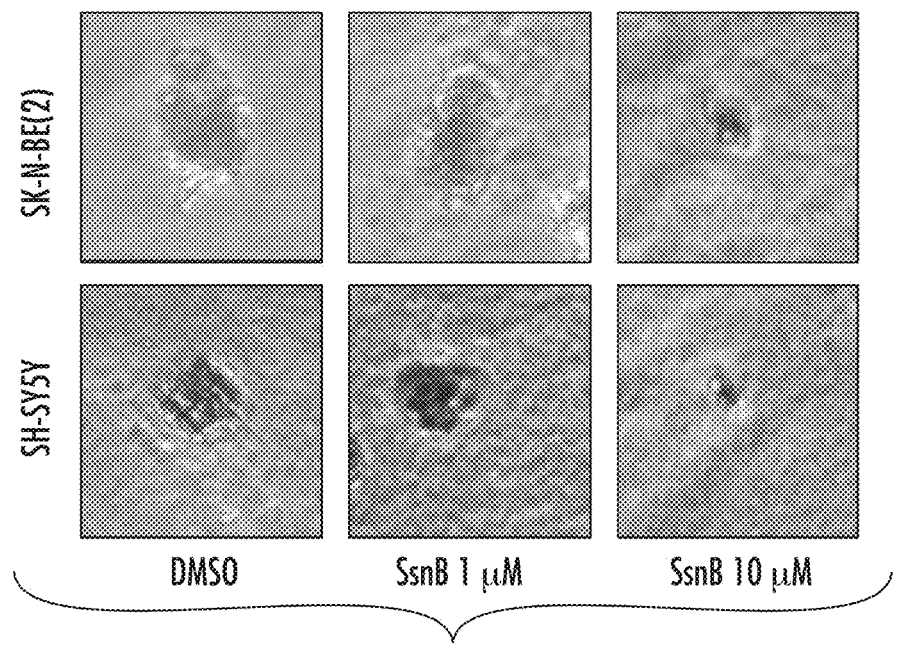
FIG. 6A are phase contrast images showing neuroblastoma colonies formed after treatment with DMSO or SsnB (1 and 10 μM) for 45 days in anchorage-independent agarose gel colony formation assay.
Figure 6B:
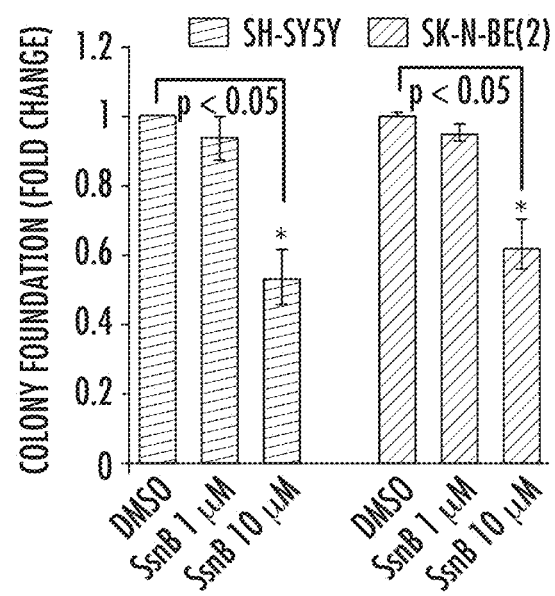
FIG. 6B graphically presents the number of colonies of FIG. 6A as counted and plotted. The bar represents mean and S.D. of three independent experiments and *$p<0.05$ was considered significant.

The anti-proliferative activity of SsnB to affects the tumor progression property of neuroblastoma cells was tested by performing two layer agarose gel colony formation assays. Agarose gel colony formation assay is an anchorage-independent in vitro cell transformation assay, and mimics the process of in vivo carcinogenesis. Neuroblastoma cells (N-myc amplified cell, SK-N-BE(2), and N-myc nonamplified cell, SH-SY5Y) were grown in agarose in presence or absence of SsnB (1 µM and 10 µM) and after 45 days the number of colonies was counted. The representative phase contrast images in FIG. 6A showed that the size of colonies in SsnB 10 µM treated samples were significantly smaller than the control and SsnB (1 µM) treated samples. The representative bar diagram demonstrated that SsnB at 10 µM concentration significantly inhibited the colony formation capability of both cells (*p<0.05, SsnB 10 µM vs control; FIG. 6B).

Figure 6C:
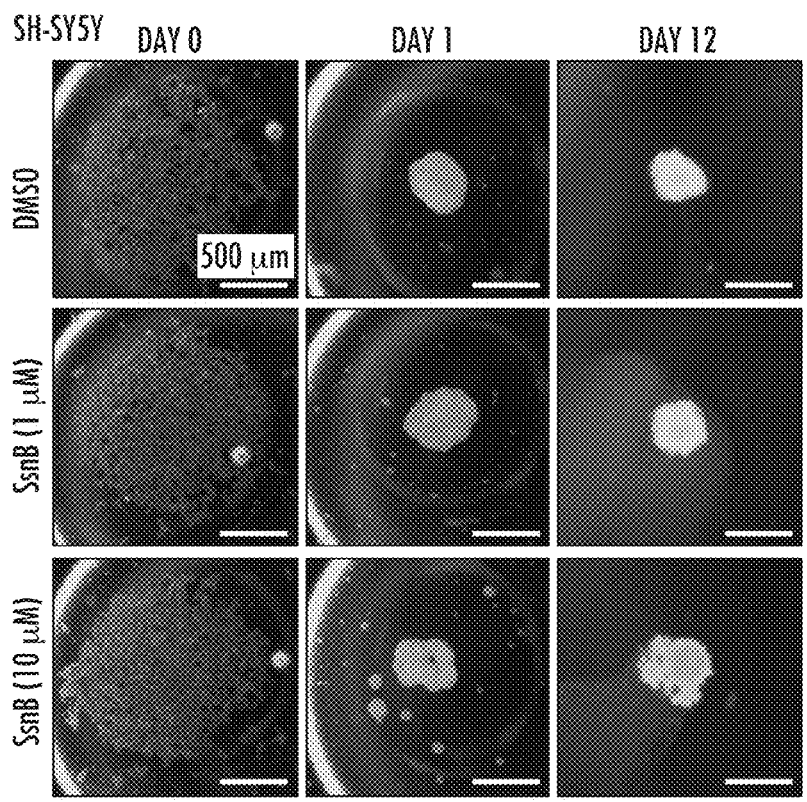
FIG. 6C and FIG. 6D are phase contrast images showing spheroid formation in absence or presence of SsnB (1 or 10 μM) in 3-D hanging drop assay. Twenty microliter drop containing 20,000 cells (SH-SY5Y (FIG. 6C); and SK-N-BE(2) cells (FIG. 6D)) were pipetted on the lower side of the lid of petri dish. The lid was gently inverted, placed on top of the petri dish and let them grow at 37° C. On day 0, day 1 and day 12 the image of cells in each droplet was taken by Olympus inverted microscope to monitor the spheroid formation. Scale bar=500 μm.
Figure 6D:
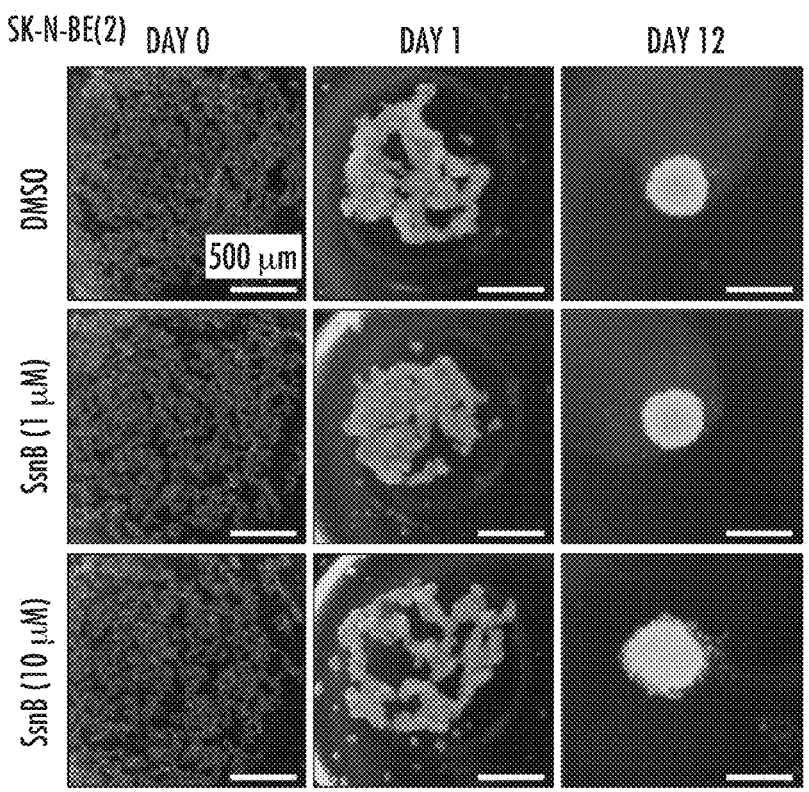

As SsnB inhibited the formation of neuroblastoma colony in anchorage-independent agarose gel assay, the ability of SsnB to inhibit the initiation of neuroblastoma tumors was tested in a hanging drop assay method. In the hanging drop assay the cells under the force of gravity and surface tension start accumulating at the bottom of the hanging drop and join together to form a spheroid. Spheroids represent an in vitro 3D tissue structure that mimics in vivo tumor tissue organization and microenvironment, and 3D culture better reflect cancer cells in their native, in vivo, environment. As shown in FIG. 6C and FIG. 6D, within 24 hours, both neuroblastoma cells (SH-SY5Y cells, C; and SK-N-BE(2) cells, D) grown in hanging drop culture started aggregating at the bottom of the droplet. On day 12, the shape of the aggregates became rounder and smoother with a gradual decrease in the radius of the spheroid, and compact cell clusters were formed in DMSO- and SsnB (1 µM)-treated SH-SY5Y and SK-N-BE(2) cells. The decrease in size is the result of higher cell-cell cohesion, which yields more compact aggregates. However, at 10 µM SsnB concentration the cells were loosely attached in spheroids suggesting that SsnB at 10 µM inhibited cell-cell attachment in both cell lines (SH-SY5Y and SK-N-BE(2) cells) as a result these cells were unable to aggregate to form compact spheroids.

EXAMPLE 2

Cell Culture

Human neuroblastoma SH-SY5Y cells were purchased from American Type Culture Collection (ATCC, Manassas, Va.). Cells were grown and maintained in complete culture medium (Dulbecco's Modified Eagle's Medium, DMEM, +10% fetal bovine serum, FBS; Atlanta Biologicals, Lawrenceville, Ga.) at 37° C. in a humidified incubator with 5% $CO_2$.

In Vivo Xenograft Neuroblastoma Mouse Model

Six-week-old female homozygous athymic nude mice (nu/nu; strain-Crl:NU-Foxn1nu) were purchased from Charles River Laboratories (Wilmington, Mass.), and housed in the University of South Carolina Animal Research Facility. All animal experiments were carried out in compliance with the National Institute of Health (NIH) guidelines and were approved by the Institutional Animal Care and Use Committee (IACUC) of the University of South Carolina. The animals were maintained at 25° C. with a 12-h light/12-h dark cycle in laminar flow cabinets under specific pathogen-free conditions and given sterile water and food ad libitum.

A neuroblastoma xenograft mice model using SH-SY5Y cells was used. To develop localized subcutaneous tumors, $2 \times 10^7$ SH-SY5Y cells were mixed 1:1 with matrigel (BD biosciences, San Jose, Calif.) to make 0.1 ml total volume, and cells were injected subcutaneously into the flank region of mice using sterile 27-gauge needle. The animal weight and general appearance were recorded regularly throughout the experiments. On every third day, tumor size was measured with calipers and tumor volume was calculated using the ellipsoid formula (length×width×height×0.5).

Tumor-bearing mice were divided into two groups—(i) control without SsnB treatment, n=4; and (ii) experimental with SsnB treatment (10 mg/kg body weight per mice), n=4. When tumor volume was reached a palpable size of about 100 mm$^3$, SsnB (10 mg/kg body weight per mice in 1 ml of PBS) was administered daily by intraperitoneal injection. Stock solution of SsnB was prepared in dimethyl sulfoxide (DMSO), and final suspension was made in 1 ml of PBS. Control mice received equal volume of only the vehicle. After 15 days of SsnB treatment, mice from all groups were euthanized. Tumors were harvested and weighed. Portions of tumors were fixed in 4% paraformaldehyde/PBS or snap frozen in liquid nitrogen for further use in biochemical assays.

Immunohistochemistry to Detect Cleaved Caspase-3 Protein Level in Tumor Tissues

Paraformaldehyde-fixed paraffin-embedded tumor sections (5 µm thick) were deparaffinized in xylene and rehydrated with sequential immersion in graded ethanol (100%, 95%, 85%, 70% and 50%). After antigen unmasking by boiling slides in sodium citrate buffer (10 mM, pH 6.0) for 30 min and permeabilization with 0.2% Triton X-100/PBS for 10 min, tissue sections were blocked with 10% immunoglobulin free-bovine serum albumin (IgG-free BSA; Jackson ImmunoResearch Laboratories, West Grove, Pa.) in 1×PBS for overnight at 4° C. Sections were incubated with antibodies raised against cleaved caspase-3 (1:100 dilution in 5% IgG-free BSA/PBS; Cell Signaling Technology, Danvers, Mass.) for overnight at 4° C. Primary antibodies were detected with secondary antibodies conjugated with fluorescein isothiocyanate (FITC) (1:4000 dilution in 5% IgG-free BSA/PBS) for 2 h at room temperature. After washing with 1×PBS for 4 times (10 min for each washing), sections were mounted with antifade Vectashield mounting media (Vector Laboratories, Burlingame, Calif.), and signals were visualized under Nikon-E600 fluorescence microscope (Nikon, Tokyo, Japan). DAPI (4',6-diamidino-2-phenylindole; Sigma-Aldrich, St. Louis, Mo.) was used to counterstain nuclei.

TUNEL Staining to Detect DNA Fragmentation in Tumor Tissues

Terminal deoxynucleotidyl transferase dUTP nick end labeling (TUNEL) was performed to detect DNA fragmentation using DeadEnd fluorometric TUNEL kit (Promega, Madison, Wis.) following manufacturer's protocol. Briefly, paraformaldehyde-fixed paraffin-embedded tumor sections (5 µm thick) were deparaffinized in xylene, rehydrated with graded ethanol (100%, 95%, 85%, 70%, 50%) and washed with 0.85% NaCl. Tissue sections were fixed with 4% paraformaldehyde/PBS and permeabilized with proteinase K solution (20 µg/ml) for 10 min. The nicked DNA was labeled with fluorescence-labeled dUTP nucleotide and terminal deoxynucleotidyl transferase enzyme mix for 60 min at 37° C. After washing with 2× standard saline citrate solution (SSC), slides were mounted with antifade Vectashield mounting media (Vector Laboratories) and examined under Nikon E-600 fluorescence microscopy. Nuclei were counterstained with DAPI (4',6-diamidino-2-phenylindole; Sigma-Aldrich, St. Louis, Mo.).

Data Analysis

Data are presented as the mean±standard deviation of at least three independent experiments. Comparisons were made among the groups using unpaired t test followed by two tail P value (GraphPad software, La Jolla, Calif.). A p-value <0.05 was considered significant.

Abbreviations b.wt., body weight; BSA, bovine serum albumin; DAPI, 4',6-diamidino-2-phenylindole; DMEM, Dulbecco's Modified Eagle's Medium; DMSO, dimethyl sulfoxide; EDTA, Ethylenediaminetetraacetic acid; FBS, fetal bovine serum; GSH, glutathione; NAC, N-acetylcystamine; O.D., optical density; PBS, phosphate buffered saline; ROS, reactive oxygen species; SDS, sodium dodecyl sulfate; SsnB, sparstolonin B; TUNEL, terminal deoxynucleotidyl transferase dUTP nick end labeling.

Results

SsnB Inhibits the Growth of Tumors In Vivo

Figure 7A:
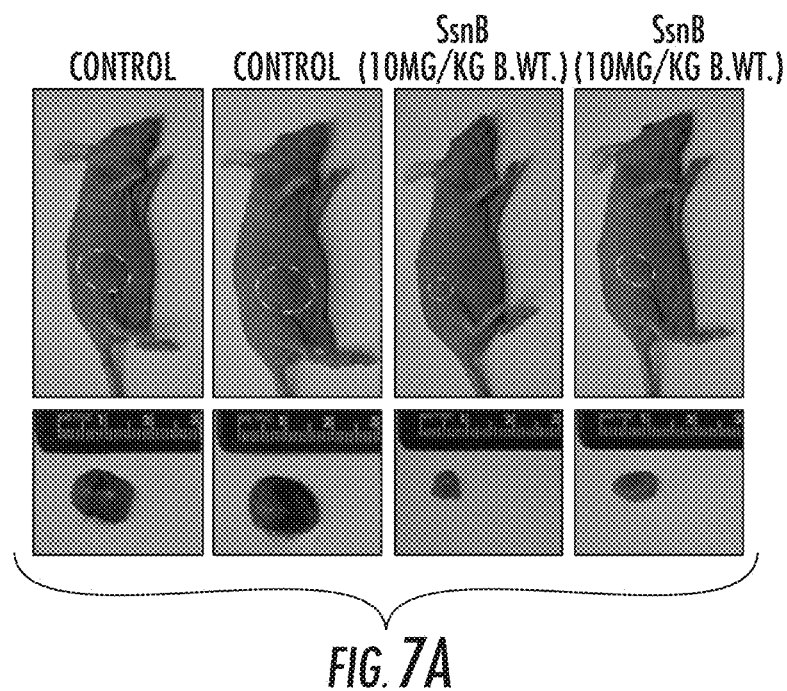
FIG. 7A shows the size of tumors in control and SsnB treated neuroblastoma xenograft mice (upper panel). Pictures were taken after 15 days of SsnB treatment. White dotted circles in the upper panels show the location of the tumor in the mice. At the end of treatment, mice from control and SsnB-treated groups were euthanized, tumors were collected and photographed (lower panel).
Figure 7B:
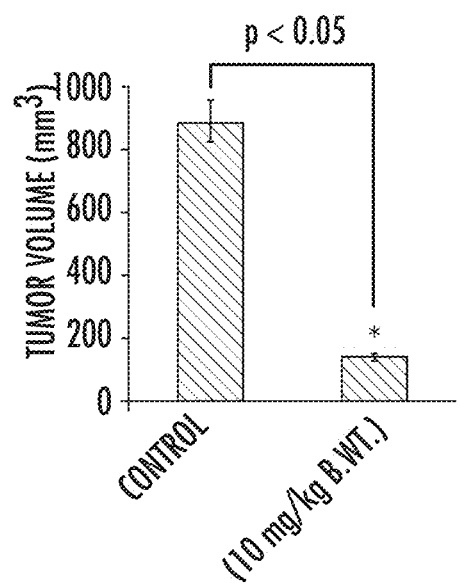
FIG. 7B is a bar diagram showing the final volume of tumors collected from control and SsnB-treated mice after 15 days treatment. *p<0.05 vs control.

In tumor-bearing mice, SsnB (10 mg/kg body weight per mouse) was administered intraperitoneally per day. At the end of the experiment, tumor in tumor-bearing mice from control and SsnB-treated groups were photographed (FIG. 7A, white dotted circle in upper panel). Mice were sacrificed, tumors were harvested and photographed (FIG. 7A, lower panel), and tumor volume was measured (FIG. 7B). FIG. 7A and FIG. 7B indicated that the average tumor size in animals receiving SsnB (10 mg/kg body weight) was significantly smaller compared to tumors in SsnB-untreated mice (*p<0.05 vs. control). The average tumor volume in control mice was 883.75±68.23 mm$^3$ and in SsnB-administered mice was 146.5±14.08 mm$^3$. These in vivo studies clearly indicated that SsnB possesses anti-tumor activity and significantly inhibited the growth of neuroblastoma tumors in xenograft mice. No toxicity of SsnB was observed as all SsnB-treated mice survived with no complications in physical appearance.

SsnB Promotes Apoptotic Cell Death in Tumors

Figure 8A:
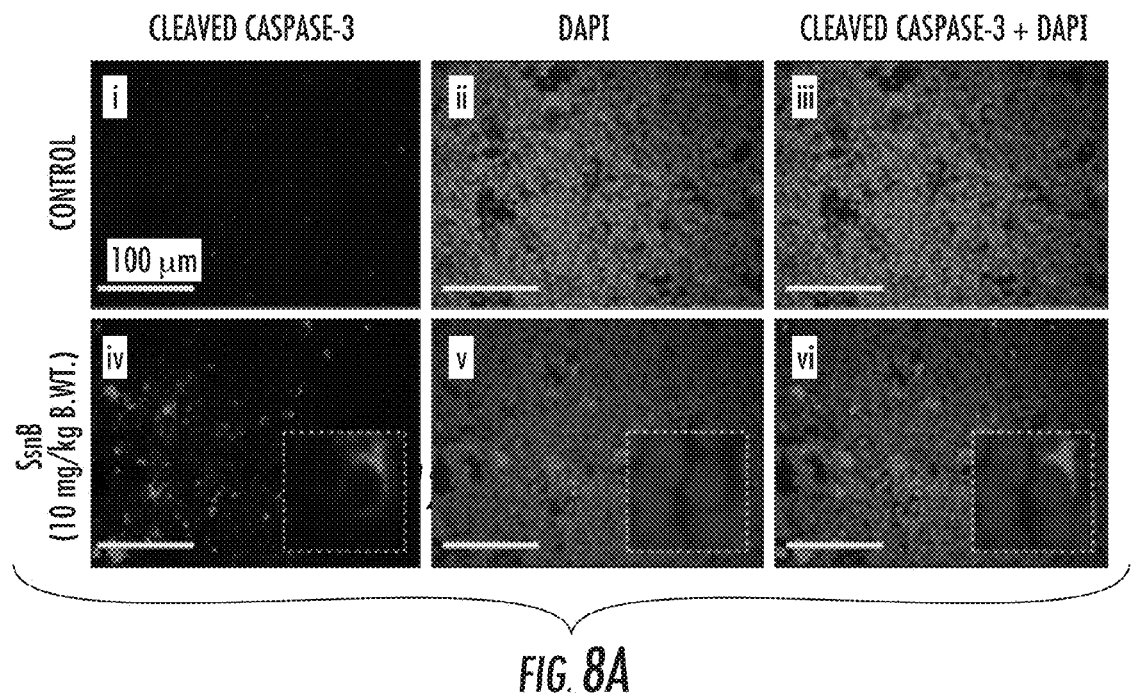
FIG. 8A presents representative immunofluorescence images showing cleaved caspase-3 staining in tumors from SsnB-treated and SsnB-untreated mice. Nuclei were counterstained with DAPI (blue). The cytoplasmic cleaved caspase-3 staining (merged and enlarged images) was observed in tumors treated with SsnB. Scale=100 μm.
Figure 8B:
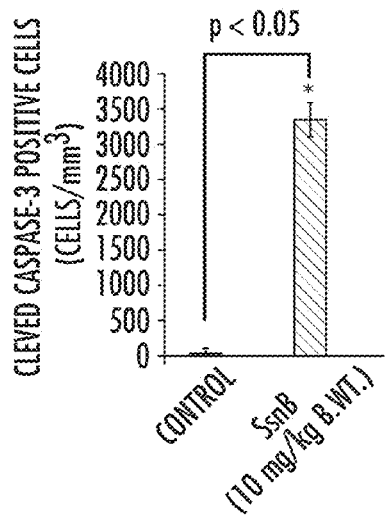
FIG. 8B is a bar diagram showing number of cleaved caspase-3 positive cells in as quantitated by ImageJ software. *p<0.05 vs control.

To determine if SsnB-inhibited tumor growth resulted from apoptotic cell death, immunohistochemistry was performed by staining the paraformaldehyde-fixed and paraffin-embedded tumor sections using antibody specific for active cleaved form of caspase-3. Cleaved caspase-3 positive cells (an indicator of apoptosis) were quantitated by ImageJ software and plotted. The representative immuno-fluorescence images in FIG. 8A demonstrated that the cleaved caspase-3 signals were significantly detected in tumors from SsnB-treated mice (FIG. 8A, iv) compared to SsnB-untreated tumors (FIG. 8A, i and FIG. 8B; *p<0.05 vs control). The cleaved caspase-3 signals were exclusively present in cytoplasm and did not overlapped with nucleus (enlarged and merged images; FIG. 8A, iv and vi).

Figure 9A:
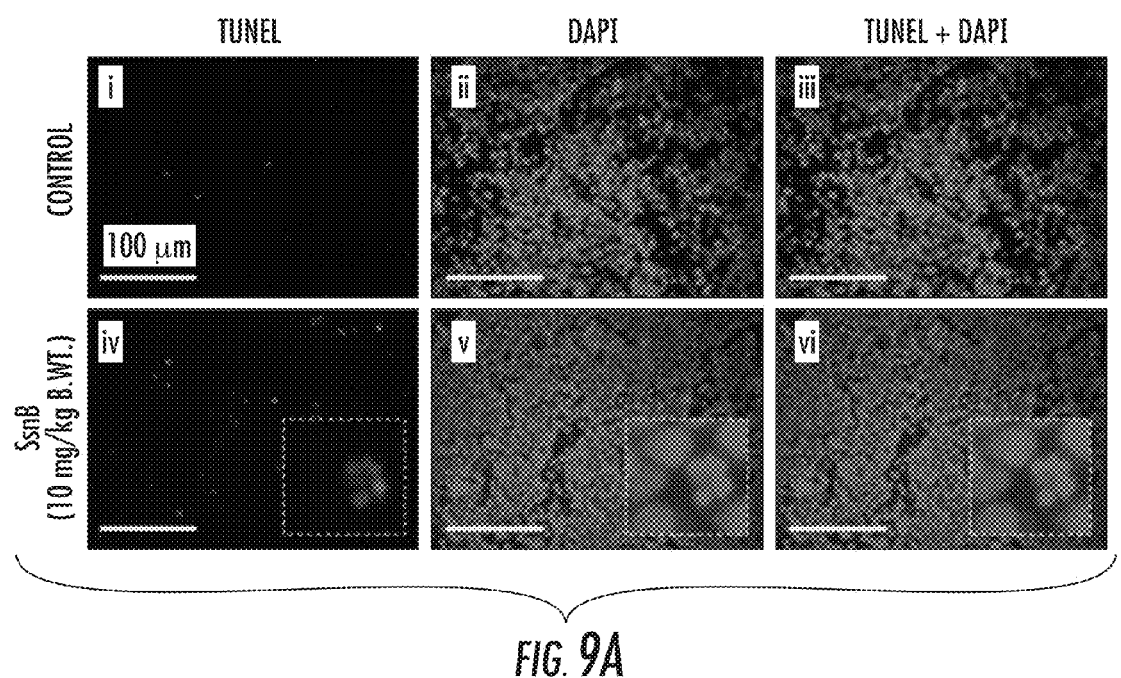
FIG. 9A presents fluorescence images showing TUNEL staining in tumors. Nuclei were counterstained with DAPI. In contrast to control tumors, TUNEL-staining (an indicator of DNA fragmentation) was significantly detected in SsnB-treated tumors, and staining was exclusively present in nucleus (merged and enlarged images). Scale=100 μm.
Figure 9B:
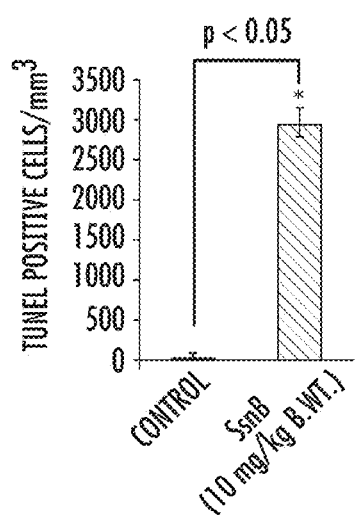
FIG. 9B is a bar diagram of the TUNEL-positive cells as obtained by counting by use ImageJ software. *p<0.05 vs control.

SsnB-induced DNA fragmentation was examined by TUNEL assay. The TUNEL positive cells (an indication of DNA fragmentation) were counted by ImageJ software and plotted. The representative images in FIG. 9A showed that compared to control, SsnB (10 mg/kg) increased the number of TUNEL positive cells (green) in SH-SY5Y tumors (compare FIG. 9A, i and iv, and FIG. 9B; *p<0.05 vs. control). The staining for nuclei and fragmented DNA (TUNEL-positive staining) overlapped in a single cell (enlarged and merged images; FIG. 9A, iv and vi) suggesting that SsnB promoted apoptosis in these cells. These results indicated that SsnB promotes apoptotic cell death to reduce tumor size in xenograft mice.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method for inhibiting the viability of neuroblastoma cells in vitro, the method comprising contacting a neuroblastoma cell culture with sparstolonin B, wherein the sparstolonin B contacts the cells at a concentration of about 10 micromolar or greater, wherein upon contact, the neuroblastoma cells exhibit cell death.

2. The method of claim 1, the neuroblastoma cells including one or more of N-myc amplified with wild p53 cells, N-myc amplified with mutated p53 cells, and N-myc non-amplified cells.

3. The method of claim 1, wherein the sparstolonin B is purified natural sparstolonin B.

4. The method of claim 1, wherein the sparstolonin B is synthetic sparstolonin B.

5. The method of claim 1, wherein the sparstolonin B is at a purity level of about 90% or greater.

6. The method of claim 1, wherein the sparstolonin B is 100% pure sparstolonin B.

7. The method of claim 1, wherein the sparstolonin B contacts the cells at a concentration of from about 10 micromolar to about 100 micromolar.

8. The method of claim 1, wherein the neuroblastoma cells comprise one or more of IMR-32 cells, NGP cells, SKN-BE(2) cells, SKNF-1 cells, or SH-SY5Y cells.

9. The method of claim 1, wherein the neuroblastoma cells comprise N-myc amplified neuroblastoma cells.

10. The method of claim 1, wherein the neuroblastoma cells comprise N-myc non-amplified neuroblastoma cells.

11. A method for treating neuroblastoma comprising delivering a composition to neuroblastoma cells of a subject in need thereof, wherein the composition consists of sparstolonin B as the sole active pharmaceutical agent, wherein upon delivery the neuroblastoma cells exhibit cell death.

12. The method of claim 11, wherein the composition is delivered to the subject at a sparstolonin dosage of from about 5 mg/kg/day to about 20 mg/kg/day.

13. The method of claim 11, wherein the composition is a solid.

14. The method of claim 13, wherein the composition is administered orally.

15. The method of claim 11, wherein the composition is a liquid.

16. The method of claim 15, wherein the composition is administered orally or parenterally.

17. The method of claim 11, wherein the composition is delivered via a timed release or sustained release delivery system.

18. The method of claim 11, wherein the method further comprises one or more of chemotherapy, radiotherapy, or surgical intervention.

* * * * *